(12) United States Patent
Baekkeskov et al.

(10) Patent No.: US 7,718,386 B1
(45) Date of Patent: May 18, 2010

(54) METHODS FOR THE DIAGNOSIS OF DIABETES

(75) Inventors: Steinunn Baekkeskov, San Francisco, CA (US); Henk-Jan Aanstoot, San Francisco, CA (US); Pietro Decamilli, Guilford, CT (US); Franco Folli, New Haven, CT (US); Michele Solimena, New Haven, CT (US)

(73) Assignees: The Regents of the University of California, Oakland, CA (US); Yale University, New Haven, CT (US)

( * ) Notice: Subject to any disclaimer, the term of this patent is extended or adjusted under 35 U.S.C. 154(b) by 0 days.

(21) Appl. No.: 08/452,053

(22) Filed: May 25, 1995

Related U.S. Application Data

(63) Continuation of application No. 08/174,550, filed on Dec. 28, 1993, now Pat. No. 5,512,447, which is a continuation of application No. 07/579,007, filed on Sep. 7, 1990, now abandoned.

(51) Int. Cl.
*G01N 33/564* (2006.01)
(52) U.S. Cl. .................. 435/7.4; 436/506; 436/811
(58) Field of Classification Search .................. 435/7.4, 435/7.71, 7.93; 436/506, 518, 811
See application file for complete search history.

(56) References Cited

U.S. PATENT DOCUMENTS

| | | | |
|---|---|---|---|
| 4,067,775 A | 1/1978 | Wurzburg et al. ............ 435/7.4 |
| 4,086,142 A | 4/1978 | Huang et al. |
| 4,736,020 A | 4/1988 | Hillen et al. |
| 4,855,242 A | 8/1989 | Soeldner ..................... 436/539 |
| 5,258,498 A | 11/1993 | Huston et al. ............... 530/350 |
| 5,512,447 A * | 4/1996 | Baekkeskov et al. ......... 435/7.4 |
| 5,645,998 A * | 7/1997 | Atkinson et al. ............. 435/7.4 |
| 5,674,978 A | 10/1997 | Tobin et al. ................. 530/326 |
| 5,762,937 A | 6/1998 | Atkinson et al. ......... 424/198.1 |
| 5,998,366 A | 12/1999 | Tobin et al. ................... 514/12 |
| 6,001,360 A | 12/1999 | Atkinson et al. ......... 424/185.1 |
| 6,277,586 B1 * | 8/2001 | Tobin et al. .................. 435/7.6 |

FOREIGN PATENT DOCUMENTS

| | | |
|---|---|---|
| EP | 383 129 A2 | 8/1990 |
| WO | WO 90/07117 | 6/1990 |
| WO | WO 90/10449 | 9/1990 |
| WO | WO 92/03733 | 3/1992 |

OTHER PUBLICATIONS

Baekkeskov et al., Nature 287:167-169, 1982.*
Baekkeskov et al., Diabetes 38:1133-1141, 1989.*
Christie et al., Diabetologia 31:597-602, 1988.*
Maggio, Ed., *Enzyme Immunoassay*, CRC Press, Inc. Boca Raton, FL, pp. 167-179, 1980.*
Bonifacio et al. Islet Cell Antigens in the Prediction and Prevention of Isulin-dependent Diabetes Mellitus, Annals of Med., 1997, 29:405-412.*
Rosenbloom et al. Therapeutic Controversy: Prevention and Treatment of Diabetes in Children, Journal of Clinical Endocrinology & Metabolism, 1999, 85(2):494-522.*
Winter et al. Immunological Markers in the Diagnosis and Prediction of Autoimmune Type 1a Diabetes, Clinical Diabetes, 2002, 20 :183-191.*
Krischer et al. Screening Strategies for the Identification of Multiple Antibody-Positive Relatives of Individuals with Type 1 Diabetes, Journal of Clinical Endocrinology & Metabolism, 2003, 88(1):103-108.*
Julien et al., "Rat Brain Glutamic Acid Decarboxylase Sequence Deduced from a Cloned cDNA," *J. Neurochem.*, 54(2):703-705 (1990).
Kalden, J.R., "Immunological Treatment of Autoimmune Disease," *Adv. Immunol.*, 68:333-418 (1998).
Kaufman et al., "Brain Glutamate Decarboxylase Cloned in λgt-11: Fusion Protein Produces γ-Aminobutyric Acid," *Science*, 232:1138-1140 (1986).
Kaufman et al., "Spontaneous loss of T-cell tolerance to glutamic acid decarboxylase in murine insulin-dependent diabetes," *Nature*, 366:69-71 (1993).
Kaufman et al., "Two Forms of the γAminobutyric Acid Synthetic Enzyme Glutamate Decarboxylase have Distinct Intraneuronal distributions and Cofactor Interactions," *J. Neurochem.*, 56(2):720-723 (1991).

(Continued)

*Primary Examiner*—Stacy B Chen
(74) *Attorney, Agent, or Firm*—Townsend and Townsend and Crew, LLP

(57) ABSTRACT

Assays for the detection of diabetes and prediabetic status rely on exposing patient serum samples to purified ligand capable of binding autoantibodies specific for a 64kD autoantigen present on pancreatic β-cells. The purified ligand is usually purified glutamic acid decarboxylase (GAD) or a fragment or analog thereof. Preferably, the assays will detect the presence of antibodies to both lower molecular weight GAD and higher molecular weight GAD since diabetic and prediabetic status may be associated with only one of these two forms. The assays can be performed using conventional protocols, such as radioimmunoassay, enzyme-linked immunosorbent assay, and enzyme assay. Methods for treating diabetes comprise administering pharmaceutical compositions including the purified ligand, particularly when coupled to an immunoglobulin or lymphoid cell to induce tolerance. Alternatively, tolerance may be induced by administering attenuated T-helper cells, or isolated T-cell receptors, where the T-helper cells have been isolated based on their reactivity with GAD or equivalent ligand.

34 Claims, 10 Drawing Sheets

OTHER PUBLICATIONS

Legay et al., "Phylogenesis of Brain Glutamic Acid Decarboxylase from Vertebrates: Immunochemical Studies," *J. Neurochem.*, 46(5):1478-1486 (1986).

Legay et al., "Evidence for two distinct forms of native glutamic acid decarboxylase in rat brain soluble extract: an immunoblotting study," *J. Neurochem.*, 48(4):1022-1026 (1987).

Lemmark, A., "Glutamic acid decarboxylase—gene to antigen to disease," *J. Int. Med.*, 240:259-277 (1996).

Lorish et al., "Stiff-Man Syndrome Updated," *Mayo Clinic Proc.*, 64:629-636 (1989).

Okada et al., "High Concentration of GABA and High Glutamate Decarboxylase Activity in Rat Pacreatic Islets and Human Insulinoma," *Science*, 194:620-622 (1976).

Petersen et al., "Treatment with GAD65 or BSA does not protect against diabetes in BB rats," *Autoimmunity*, 25:129-138 (1997).

Petersen et al., "Neonatal Tolerization With Glutamine Acid Decarboxylase But Not With Bovine Serum Albumin Delays the Onset of Diabetes in NOD Mice," *Diabetes*, 44:1478-1484 (1994).

Sinha et al., "Autoimmune Diseases: the Failure of Self Tolerance," *Science*, 248:1380-1388 (1990).

Solimena et al., "Autoantibodies to GABA-ergic neurons and pancreatic beta cells in Stiff-Man syndrome," *New England J. Med.*, 322(22):1555-1560 (1990).

Solimena et al., "Autoantibodies to glutamic acid decarboxylase in a patient with Stiff-Man syndrome, epilepsy, and type I diabetes mellitus," *New England J. Med.*, 318(16):1012-1020 (1988).

Tian et al., "Modulating autoimmune responses to GAD inhibits disease progression and prolongs islet graft survival in diabetes-prone mice," *Nature Med.*, 2(12):1348-1353 (1996).

Tisch et al., "Immune response to glutamic acid decarboxylase correlates with insulitis in non-obese diabetic mice," *Nature*, 366:71-75 (1993).

Tisch et al., "Antigen-specific immunotherapy: is it a real possibility to combat T-cell-mediated autoimmunity," *PNAS*, 91:437-438 (1994).

Urban et al., "Restricted Use of T Cell Receptor V Genes in Murine Autoimmune Encephalomyelitis Raises Possibilities for Antibody Therapy," *Cell*, 54:577-592 (1988).

Vandenbark et al., "Immunization with a synthetic T-cell receptor V-region peptide protects against experimental autoimmune encephalomyelitis," *Nature*, 341:541-544 (1989).

Vincent et al., "Immunohistochemical Studies of then GABA System in the Pancreas," *Neuroendocrinology*, 36:197-204 (1983).

Wraith et al., "Antigen Recognition in autoimmune Encephalomyelitis and the Potential for Peptide-Mediated Immunotherapy," *Cell*, 59:247-255 (1989).

Wyborski et al., "Characterization of a cDNA coding for rat glutamic acid decarboxylase," *Molec. Brain Res.*, 8:193-198 (1990).

Atkinson et al., "M, 64,000 Autoantibodies (64KA) Predict Insulin Dependent Diabetes," *American Diabetes Assoc. 48th Ann. Mtng.*, abstract # 391 (1988).

Bergenholt et al., "A new model for analyzing immunomodulation of T cell responses induced by oral administration of islet cell antigens," *Ann. Rev. NY Acad. Sci.*, 958:179-181 (2002).

Butler et al., "Identification of a Dominant Epitope of Glutamic Acid Decarboxylase (GAD-65) Recognized by Autoantibodies in Stiff-Man Syndrome," *J. Exp. Med.*, 178(6):2097-2106 (1993).

Christgau et al., "Pancreatic β Cells Express Two Autoantigenic Forms of Glutamic Acid Decarboxylase, a 65-kDa Hydrophilic Form and a 64-kDA Amphiphilic Form Which Can Be Both Membrane-bound and Soluble", *J. Biol. Chem.*, 266(31):21257-21264 (1991).

Christgau et al., "Membrane Anchoring of the Autoantigen $GAD_{65}$ to Microvesicles in Pancreatic β-cells by Palmitoylation in the $NH_2$-Terminal Domain," *J. Cell Biology*, 118(2):309-320 (1992).

Christie et al., "Distinct Antibody Specificities to a 64-kD Islet Cell Antigen in Type I Diabetes as Revealed by Trypsin Treatment," *J. Exp. Med.*, 172:789-794 (1990).

Christie et al., "Detection of Pancreatic Islet 64,000 M, Autoantigens in Insulin-dependent Diabetes Distinct from Glutamate Decarboxylase," *J. Clin. Invest.*, 92:240-248 (1993).

Christie et al., "Antibodies to GAD and tryptic fragments of islet 64K antigen as distinct markers for development of IDDM. Studies with identical twins," *Diabetes*, 41(7):782-787 (1992).

Goodnow, C., "Pathways for self-tolerance and the treatment of autoimmune diseases," *Lancet*, 357:2115-2121 (2001).

Hagopian et al., "Autoantibodies in IDDM primarily recognize the 65,000-M® rather than the 67,000-M® isoform of glutamic acid decarboxylase," *Diabetes*, 42(4):631-636 (1993).

Hampe et al., "Recognition of glutamic acid decarboxylase (GAD) by autoantibodies from different GAD antibody-positive phenotypes," *J. Clin. Endocrinology & Metabolism*, 85(12):4671-4679 (2000).

Jun et al., "Prevention of autoimmune diabetes by immunogene therapy using recombinant vaccinia virus expressing glutamic acid decarboxylase," *Diabetologia*, 45(5):668-676 (2002).

Kanaani et al., "A combination of three distinct trafficking signals mediates axonal targeting and presynaptic clustering of GAD65," *J. Cell Biol.*, 158(7):1229-1238 (2002).

Karlsen et al., "Recombinant glutamic acid decarboxylase (representing the single isoform expressed in human islets) detects IDDM-associated 64,000-M® autoantibodies," *Diabetes*, 41(10):1355-1359 (1992).

Karlsen et al., "Cloning and primary structure of a human islet isoform of glutamic acid decarboxylase from chromosome 10," *PNAS*, 88:8337-8341 (1991).

Kim et al., "Higher Autoantibody Levels and Recognition of a Linear $NH_2$-terminal Epitope in the Autoantigen $GAD_{65+}$Distinguish Stiff-Man Syndrome from Insulin-dependent Diabetes Mellitus," *J. Exp. Med.*, 180:595-606 (1994).

Kim et al., "Differential expression of GAD65 and GAD67 in human, rat, and mouse pancreatic islets," *Diabetes*, 42(12):1799-1808 (1993).

Lan et al., "IA-2, a transmembrane protein of the protein tyrosine phosphate family, is a major autoantigen in insulin-dependent diabetes mellitus," *PNAS*, 93:6367-6370 (1996).

Marketletter Publications, Ltd., "AutoImmune shares collapse on Colloral data in rheumatoid arthritis," pp. 1-2, Sep. 13, 1999.

Passini et al., "The 37 / 40-kilodalton autoantigen in insulin-dependent diabetes mellitus is the putative tyrosine phosphate 1A-2," *PNAS*, 92:9412-9416 (1995).

Payton et al., "Relationship of the 37,000- and 40,000-M, Tryptic Fragments of Islet Antigens in Insulin-dependent Diabetes to the Protein Tyrosine Phosphatase-like Molecule 1A-2 (ICA512)," *J. Clin. Invest.*, 96:1506-1511 (1995).

Petersen et al., "Differential expression of glutamic acid decarboxylase in rat and human islets," *Diabetes*, 42(3):484-495 (1993).

Solimena et al., "Autoimmunity to glutamic acid decarboxylase (GAD) in Stiff-man syndrome and insulin-dependent diabetes mellitus," *Trends in Neurosciences*, 14(10):452-457 (1991).

Tian et al., "Nasal administration of glutamate decarboxylase (GAD65) peptides induces Th2 responses and prevents murine insulin-dependent diabetes," *J. Exp. Med.*, 183(4):1561-1567 (1996).

Tisch et al., "Induction of glutamic acid decarboxylase 65-specific Th2 cells and suppression of autoimmune diabetes at late stages of disease is epitope dependent," *J. Immunology*, 163(3):1178-1187 (1999).

Wilson et al., "Therapeutic alteration of insulin-dependent diabetes mellitus progression by T cell tolerance to glutamic acid decarboxylase 65 peptides in vitro and in vivo," *J. Immunology*, 167(1):569-577 (2001).

Areshev et al., "Structure of Glutamate Decarboxylase and Related PLP-Enzymes: Computer-graphical Studies," *J. Biomolecular Structure and Dynamics*, 18(1):127-136 (2000).

Atkinson et al., "The NOD mouse model of type 1 diabetes: as good as it gets?," *Nature Med.*, 5(6):601-604 (1999).

Atkinson et al., "64,000 $M_r$ autoantibodies as predictors of insulin-dependent diabetes," *The Lancet*, 335:1357-1360 (1990).

Baekkeskov et al., "Identification of the 64K autoantigen in insulin-dependent diabetes as the GABA-synthesizing enzyme glutamic acid decarboxylase," *Nature*, 347:151-156 (1990).

Baekkeskov et al., "Antibodies to a 64,000 $M_r$ Human Islet Cell Antigen Precede the Clinical Onset of Insulin-dependent Diabetes," *J. Clin. Invest.*, 79:926-934 (1987).

Braley-Mullen, H., "Activation of distinct subsets of T supressor cells with Type III pneumococca polysaccharide coupled to syngeneic spleen cells," *Annals of NY Acad. Sci.*, 392:156-166 (1982).

Benjmini et al., *Immunology, A short Course*, Alan Liss, Inc., New York, NY, p. 256.

Chang et al., "Characterization of the Proteins Purified with Monoclonal Antibodies to Glutamic Acid Decarboxylase," *J. Neurosci.*, 8(6):2123-2130 (1988).

Christie et al., "Cellular and subcellular localization of an Mr 64,000 protein autoantigen in insulin dependant diabetes," *J. Biol. Chem.*, 265(1):376-381 (1990).

Dorf et al., "Suppressor cells and immunosuppression," *Ann. Rev. Immunol.*, 2:127-158 (1984).

Erlander et al., "Two genes encode distinct glutamate decarboxylase," *Neuron*, 7:91-100 (1991).

Garry et al., "Cellular and Subcellular Immunolocalization of L-Glutamate Decarboxylase in Rat Pancreatic Islets," *J. Histochem. Cytochem*, 36(6):573-580 (1988).

Harrison, L.C., "Antigen-specific therapy for autoimmune disease: prospects for the prevention of insulin-dependent diabetes," *Molecular Med.*, 1:722-727 (1995).

Howell et al., "Vaccination Against Experimental Allergic Encephalomyelitis with T-cell Receptor Peptides," *Science*, 246:668-670 (1989).

Janeway, C.A., "Immunotherapy by peptides?," *Nature*, 341:482-483 (1989).

* cited by examiner

| | n | 65K NEG −<br>67K NEG − | 65K POS +<br>67K NEG − | 65K NEG −<br>67K POS + | 65K POS +<br>67K POS + |
|---|---|---|---|---|---|
| CONTROL | 10 | 10 | 0 | 0 | 0 |
| NEW IDDM | 26 | 2 | 7 | 3 | 14 |
| PRE IDDM | 14 | 2 | 5 | 0 | 7 |
| SMS | 8 | 0 | 0 | 0 | 8 |

FIG. 8.

METHODS FOR THE DIAGNOSIS OF DIABETES

CROSS-REFERENCE TO RELATED APPLICATIONS

This application is a continuation of Ser. No. 08/174,550 (now U.S. Pat. No. 5,512,447), filed Dec. 28, 1993 which is a continuation of Ser. No. 07/756,207 filed on Sep. 6, 1991 which is a continuation-in-part of Ser. No. 07/579,007 filed on Sep. 7, 1990. The disclosure of Ser. No. 07/579,007 is incorporated herein by reference.

This invention was made with Government support under Grant No. DK 41822-01 awarded by the National Institutes of Health and Contract No. 1 ROI A130248-01 awarded by the National Institutes of Health, National Institute of Infectious and Allergic Diseases. The Government has certain rights in this invention.

BACKGROUND OF THE INVENTION

1. Field of the Invention

The present invention relates generally to improved methods for identifying and treating individuals who suffer from or are susceptible to diabetes. More particularly, the present invention relates to the use of glutamic acid decarboxylase to detect pancreatic β-cell specific autoantibodies in sera of diabetic or prediabetic individuals and inhibit the immune response which causes β-cell destruction.

Insulin dependent diabetes mellitus (IDDM) primarily afflicts young people. Although insulin is available for treatment, the several fold increased morbidity and mortality associated with this disease urge the development of early diagnostic and preventive methods. The destruction of pancreatic β-cells, which precedes the clinical onset of IDDM, is mediated by autoimmune mechanisms. Among the most thoroughly studied autoimmune abnormalities associated with the disease is the high incidence of circulating β-cell specific autoantibodies at the time of diagnosis. Family studies have shown that the autoantibodies appear prior to overt IDDM by a number of years, suggesting a long prodromal period of humoral autoimmunity before clinical symptoms emerge. The family studies have also documented a slow, progressive loss of insulin response to intravenous glucose in the years preceding diagnosis. The presence of β-cell specific autoantibodies in the prediabetic period is likely to reflect the ongoing autoimmune process, one that eventually leads to critical β-cell depletion and insulin dependency. It has been estimated that only 10% of the total β-cell mass remains at the time of clinical onset.

A major goal of diabetes research has been to develop immune interventions that block or inhibit the destruction of β-cells and development of IDDM. Since immune interventions will probably always confer some risk of untoward side effects, highly sensitive, specific and easily applicable markers for the prediabetic stage are needed if such a treatment is to become an acceptable alternative to replacement therapy with insulin.

In addition to preventative treatment, methods for early and accurate identification of susceptible individuals are needed. Assays that can detect autoantibodies associated with early humoral autoimmunity accompanying β-cell destruction are particularly desirable. The classical method for detecting islet cell autoantibodies is by immunohistology using frozen pancreatic sections. Family studies, however, have shown that the β-cell cytoplasmic antibodies (ICCA) measured by this method are of insufficient specificity to serve as a single marker of susceptibility. Moreover, ICCA are very difficult to standardize and interpretation of the stained section is subject to observer bias. Thus, there has been no way to define what is a "positive" specimen. More accurate assays may be achieved by employing more specific markers, either alone or in combination with ICCA. Alternative markers include 64 k autoantibodies, insulin autoantibodies, and MHC class II DR/Dβ haplotype.

Assays for the early detection of humoral responses in IDDM should provide a rapid and quantitative measurement of the particular marker, preferably by conventional serum assay protocols, such as enzyme linked immunosorbent assay (ELISA) and/or a radioimmunoassay (RIA). Such assays should detect a primary β-cell target antigen characteristic of humoral autoimmunity and should have improved sensitivity and specificity relative to the ICCA assay in predicting IDDM. Insulin and the 64 k β-cell autoantigen are currently the only known potential primary target antigens of humoral autoimmunity in IDDM, if β-cell expression and specificity are applied as criteria for such an antigen. Insulin autoantibodies have an incidence of only 30-40% in young children, and much lower in older children and adults, who develop IDDM. The 64 k autoantibodies have an incidence of about 80% both at the time of clinical onset and in the prediabetic period and have been shown to precede overt IDDM by several years in familial studies and to be detected concomitantly with and sometimes before, but never later than ICCA and IAA. Thus, the detection of 64 k autoantibodies promises to be a useful approach for early detection of IDDM.

Detection of the 64 kD autoantigen, however, has been problematic. The 64 kD autoantigen was heretofore only identified in the pancreatic β-cell, and has not been purified in sufficient quantities to allow sequencing, cloning, or other identification which would have permitted large scale preparation of reagents necessary for detection or therapy. For these reasons, detection of the 64 k autoantibody has been by immunoprecipitation with detergent lysates of rat and human islets. Such assays are expensive, time consuming and not easily adapted to clinical laboratory settings. Therefore, they would not be suitable for widespread screening of human populations to identify individuals at risk for developing IDDM.

For these reasons, it would be desirable to identify the nature of the 64 kD autoantigen so that large quantities of the autoantigen or analogs thereof could be obtained for use as reagents in detection and therapy of IDDM.

2. Description of the Relevant Art

The 64 kD autoantigen in pancreatic β-cells was identified originally as a target of autoantibodies in IDDM by immunoprecipitation experiments using detergent lysates of human islets (Baekkeskov et al. (1982) Nature 298:167-169). Antibodies to the 64 kD autoantigen precede the clinical onset of IDDM and have been shown to have an incidence of about 80% at clinical onset and during the prediabetic period (Baekkeskov et al. (1987) J. Clin. Invest. 79:926-934; Atkinson et al. (1990) Lancet 335:1357-1360; and Christie et al. (1988) Diabetologia 31:597-602). The rat and human 64 kD protein are highly homologous with regard to autoantigenic epitopes (Christie et al. (1990) J. Biol. Chem. 265:376-381). The 64 kD autoantigen in islets of Langerhans is detected in three different forms with regard to hydrophobicity and compartmentalization: a hydrophilic soluble form of 65 kD and pI of approximately 7.1; a 64 kD hydrophobic form, which is soluble or of a low membrane avidity and has a pI of approximately 6.7; and a hydrophobic firmly membrane anchored form of the same electrophoretic mobility and pI. Both the membrane bound and the soluble hydrophobic 64 kD forms exist as two isoforms, α and β, which have identical pI and hydrophobic properties but differ by approximately 1 kD (Baekkeskov et al. (1989) Diabetes 38:1133-1141). The 64 kD autoantigen was found to be β-cell specific in an analysis of a number of tissues, which did not include the brain (Christie et al., supra.).

Patients with a rare but severe neurological disease, Stiff Man Syndrome (SMS), have autoantibodies to GABA-ergic neurons. Glutamic acid decarboxylase (GAD), the enzyme that synthesizes GABA from glutamic acid, was found to be the predominant autoantigen (Solimena et al. (1988) N. Engl. J. Med. 318:1012-1020 and Solimena et al. (1990) N. Engl. J. Med. 322:1555-1560). Almost all the GABA-ergic neuron autoantibody positive patients were also positive for islet cell cytoplasmic antibodies, as demonstrated by immunofluorescence of pancreatic sections, and one third had IDDM. In addition, autoantibodies to GABA-ergic neurons, detectable by immunocytochemistry, were detected in 3 of 74 IDDM patients without SMS (Solimena et al. (1988) supra. and Solimena et al. (1990) supra.). Other studies have also reported a high incidence of IDDM in SMS patients (Lorish et al. (1989) Mayo Clin. Proc. 64:629-636). GAD is found at high levels in islets of Langerhans (Okada et al. (1976) Science 194:620-622). Within the islet, GAD is selectively localized to β-cells and absent in the other three endocrine cell types, the α, δ, and PP cells (Garry et al. (1988) J. Histochem. & Cytochem. 36:573-580 and Vincent (1983) Neuroendocrinol. 36:197-204). While little is known about the biochemical properties of pancreatic GAD, the brain protein has been partially characterized. In the rat brain, 60% of the protein was found to be membrane bound and 40% was soluble following homogenization (Chang and Gottlieb (1988) J. Neurosci. 8:2123-2130). GAD in brain consists of at least two isomers resolved by differences in electrophoretic mobility in SDS-PAGE. Their molecular weights have been described as 59-66 kD (Chang and Gottlieb, supra.). Immunogenic epitopes of both isoforms are highly conserved from rodents to humans (Legay et al. (1986) J. Neurochem. 46:1478-1486). The mRNA of the larger form has been cloned and sequenced (Kaufman et al. (1986) Science 232: 1138-1140 and Julien et al. (1990) J. Neurochem. 54:703-705. The protein is detected in a dimer form under non-reducing conditions (Legay (1987) J. Neurochem. 48:1022-1026). Erlander et al. (1991) Neuron 7:91-100 describes the cloning and sequencing of both the higher and lower molecular weight forms of rat CNS GAD. Cram et al. (1991) describes the partial sequencing of the brain and pancreatic forms of human GAD and reports seven amino acid substitutions over a 180 amino acid sequence. The sequence of the gene encoding the higher molecular weight form of rat CNS GAD is reported in Julien et al. (1990) J. Neurochem. 54:703-705. Portions of the experimental work underlying the present invention were reported in Baekkeskov et al. (1990) Nature 347:151-156.

SUMMARY OF THE INVENTION

According to the present invention, improved methods for diagnosing and monitoring diabetic and prediabetic individuals comprise exposing a serum sample from a patient to purified ligand capable of specifically binding autoantibodies reactive with an approximately 64 kD pancreatic β-cell autoantigen(s) (commonly referred to as the 64 kD autoantigen, but in fact comprising two distinct molecular weight forms as described below) and detecting complex formation between the ligand and the autoantibodies. The purified ligand is usually glutamic acid decarboxylase (GAD) or a fragment thereof, but may also be other ligands, such as anti-idiotypic antibodies specific for the binding region of the autoantibodies or peptides mimicking the epitopic region(s) of glutamic acid decarboxylase which binds to the autoantibodies. Preferably, the methods will detect the presence of autoantibodies to both a lower molecular form of GAD and a higher molecular weight form of GAD, more preferably distinguishing between the presence of antibodies reactive with each form.

In contrast to previous methods for detection of autoantibody to the pancreatic antigen, which have generally required the use of lysed pancreatic islet cells, use of purified ligand capable of specifically binding to the autoantibodies allows performance of a wide variety of convenient assay protocols capable of detecting the autoantibodies even at very low concentrations. Exemplary assay protocols include solid phase assays employing immobilized ligand capable of capturing the autoantibody, where the amount of captured antibody may be measured competitively or non-competitively. Exemplary competitive assays include radioimmunoassays (RIA) and enzyme-linked immunosorbent assays (ELISA) while exemplary non-competitive assays include sandwich assays. Alternatively, homogeneous assay protocols may be employed where binding of the autoantibody to a labelled ligand complex results in modulation of a signal from the complex, e.g., modulation of the activity of an enzyme label. Also useful will be enzyme assays where determination of GAD activity is used as a direct measure of autoantibody present in sera.

In another aspect, the present invention comprises compositions and methods for the treatment and prevention of diabetes by administration of a protective amount of purified ligand capable of immunologically mimicking at least a portion of the 64 kD pancreatic β-cell autoantigen. In order to induce a protective immune response (i.e., tolerance of the 64 kD autoantigen), it may be desirable to couple the ligand to immunoglobulins or lymphoid cells prior to administering to the patient.

In yet another aspect of the present invention, GAD or an equivalent ligand can be used to stimulate and isolate the T-helper cells involved in the humoral response which produces the 64 k autoantibodies. The isolated T-cell receptors on such cells may, in turn, be administered to a patient as an immunopreventive therapy.

BRIEF DESCRIPTION OF THE DRAWINGS

FIG. 8 is a chart illustrating the pattern of autoantibody reactivity with the higher and lower molecular weight forms of GAD in diabetic patients, prediabetic patients, patients suffering from stiff man syndrome, and controls.

DESCRIPTION OF THE SPECIFIC EMBODIMENTS

The present invention results from our discovery that the 64 kD autoantigen of pancreatic β-cells (which are the insulin-secreting cells of the islets of Langerhans) is glutamic acid decarboxylase (GAD) (E.C. 4.1.1.15) which is an abundant protein of GABA-secreting neurons in the central nervous system (CNS). In particular, it has been discovered that the pancreatic forms of GAD are substantially identical to and immunologically cross-reactive with the CNS forms of GAD (as described in more detail below), allowing the use of reagents incorporating either pancreatic or CNS GAD, or portions thereof, for the detection of autoantibodies to the 64 kD autoantigen (referred to herein as 64 kD autoantibodies) which have been associated with insulin dependent diabetes mellitus (IDDM), as discussed in detail hereinabove. Thus, for the first time, purified reagents suitable for conventional sera screening assays are available so that large populations may be screened for diabetes and prediabetic status in an efficient and cost-effective manner.

Figure 6:
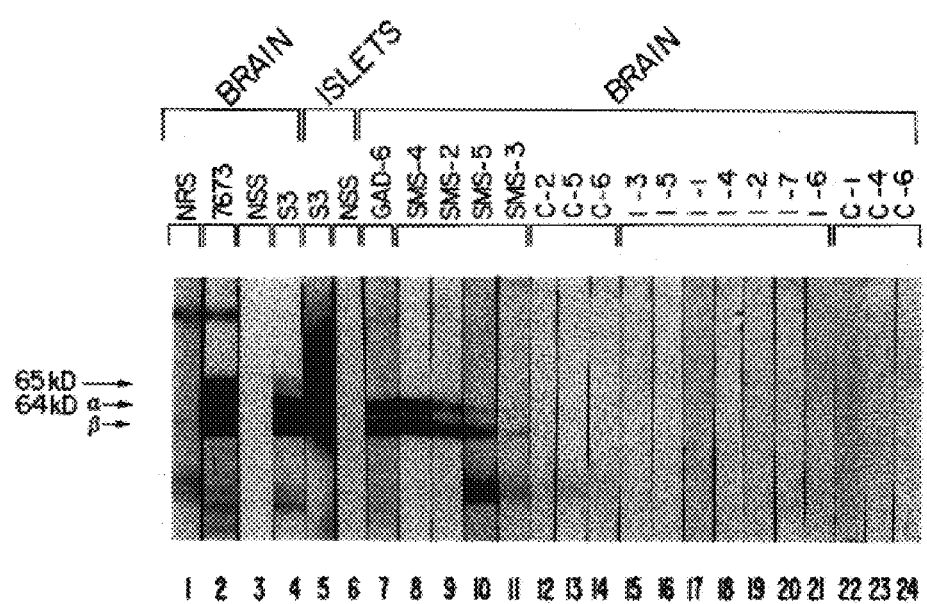
FIG. 6 includes a Western blot of neonatal rat brain and islet cells probed with glutamic acid decarboxylase antibody positive sera and diabetic sera.
Figure 7A:
FIG. 7 includes micrographs showing nerve terminals stained with the same sera, demonstrating the identity of a glutamic acid decarboxylase and the 64 kD autoantigen.
Figure 7B:
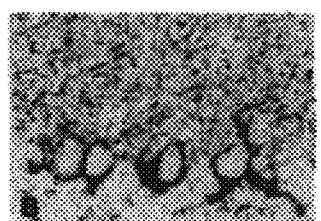
Figure 7C:
Figure 7D:
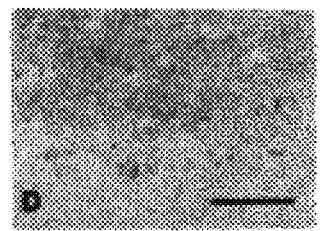

CNS GAD and pancreatic GAD are found in at least two different molecular weight forms, including a smaller form described in the literature (for CNS GAD) as having a molecular weight ranging from about 59 to 65 kD and a larger form described as having a molecular weight ranging from about 63 to 67 kD. See, Kaufman et al. (1986) Science 232: 1138-1140 and Chang and Gottlieb (1988) J. Neurosci. 8:2123-2130, the disclosures of which are incorporated herein by reference. The lower molecular weight form of both pancreatic and CNS GAD may be recognized by GAD-6 antibody, as described in Chang and Gottlieb (1988), supra. Pancreatic GAD, i.e., the 64 kD pancreatic antigen, is present as a protein doublet with electrophoretic mobility similar to that of the isoforms of brain GAD (FIG. 6). See, Baekkeskov et al. (1989) Diabetes 38:1133-1141, the disclosure of which is incorporated herein by reference. Purified compositions useful in the present invention may be obtained or derived from either or both molecular weight forms of CNS GAD or pancreatic GAD. Purified compositions from the pancreatic form of GAD can be isolated and characterized fully using CNS GAD as a starting point. Moreover, the forms of GAD are highly conserved among species, and purified ligand utilized in the present invention may be based on non-human, as well as human forms of GAD, such as rat, feline, and other forms which have been previously characterized.

More detailed characteristics of the lower molecular weight and higher molecular weight forms of pancreatic GAD are provided in the Experimental section hereinafter. Specifically, it is shown that the CNS and pancreatic forms of GAD are substantially identical for both the lower molecular weight and higher molecular weight forms. Thus, the CNS and pancreatic forms of GAD can be used interchangeably in the methods of the present invention, although natural GAD isolated from animal sources is available in quantity only from CNS cells.

The data in the Experimental section further demonstrate that recombinantly produced rat GAD is suitable for detecting the 64 kD autoantibodies in humans. Thus, the animal source of the GAD utilized in the assays does not appear to be critical. The molecular weight form of the GAD utilized to detect the autoantibodies, however, is an important aspect of the present invention, as described in more detail below.

The methods of the present invention employ purified ligand for the 64 kD autoantibodies for detection of such autoantibodies in serum samples. The purified ligand will usually be an isolated form of CNS GAD or a recombinantly-produced form of CNS GAD or pancreatic GAD, but may also be a GAD fragment or other peptide which defines an epitopic binding site capable of specifically binding the 64 k autoantibodies. It will be appreciated that knowledge of the DNA sequence of the GAD gene as well as the amino acid sequence of GAD allow identification and preparation of a variety of synthetic peptide compositions which can be utilized as the purified ligand of the present invention. Additionally, the methods of the present invention could utilize anti-idiotypic antibodies capable of specifically binding the 64 k autoantibodies.

The purified ligand of the present invention may be natural, i.e., intact CNS or pancreatic GAD or fragments thereof, isolated from suitable sources, such as human or non-human CNS and pancreatic cells. Methods for such isolation are described in Oertel et al. (1980) Brain Res. Bull. Vol. 5, Suppl. 2, pp 713-719; Oertel et al. (1981) J. Neurosci. 6:2689-2700; and Chang and Gottlieb (1988) J. Neurosci. 8:2123-2130, the disclosures of which are incorporated herein by reference. Usually, natural polypeptides will be isolated from CNS cells where GAD is more abundant than in pancreatic cells.

Natural polypeptides may be isolated by conventional techniques such as affinity chromatography. Conveniently polyclonal or monoclonal antibodies may be raised against previously-purified GAD and may be utilized to prepare a suitable affinity column by well known techniques. Such techniques are taught, for example, in Hudson and Hay, Practical Immunology, Blackwell Scientific Publications, Oxford, United Kingdom, 1980, Chapter 8. Usually, an intact form of GAD will be obtained by such isolation techniques. If peptide fragments are desired, they may be obtained by chemical or enzymatic cleavage of the intact molecule.

As an alternative to isolating intact GAD from natural sources, it will be possible to prepare synthetic proteins and polypeptides based on the sequences of the two molecular weight forms of CNS and/or pancreatic GAD. Peptide sequences from the lower molecular weight form of CNS GAD are reported in Chang and Gottlieb (1988), supra. The nucleic acid sequences of the lower molecular weight form of CNS GAD and/or pancreatic GAD may be obtained by conventional techniques using a nucleic acid probe based on the DNA sequence of the higher molecular weight form of CNS GAD which is reported in Julien et al. (1990) J. Neurochem. 54:703-705, the disclosure of which is incorporated herein by reference. Alternatively, cDNA expression libraries may be screened for a desired form of GAD using α-GAD antibodies which are available or may be prepared as described hereinbelow.

Cloning and expression of the two molecular weight forms of rat CNS GAD are described in Erlander et al. (1991) Neuron 7:91-100, where it is disclosed that the two forms are encoded by distinct genes. Cloning and expression of the higher molecular weight forms of rat pancreatic GAD is described in the Experimental section hereinafter.

Synthetic proteins and polypeptides may be produced by either of two general approaches. First, polypeptides having up to about 150 amino acids, usually having fewer than about 100 amino acids, and more usually having fewer than about 75 amino acids, may be synthesized by the well known Merrifield solid-phase synthesis method where amino acids are sequentially added to a growing chain. See, Merrifield (1963) J. Am. Chem. Soc. 85:2149-2156. Apparatus for automatically synthesizing such polypeptides using the solid-phase methodology are now commercially available from numerous suppliers, such as Applied Biosystems, Foster City, Calif.

The second and preferred method for synthesizing the proteins and polypeptides of the present invention involves the expression in cultured mammalian cells of recombinant DNA molecules encoding the desired GAD gene or portion thereof. The use of mammalian expression systems, such as Chinese hamster ovary (CHO) cells, can provide for post-translational modification of the proteins and polypeptides which enhances the immunological similarity of the synthetic products with the native forms of GAD. The GAD gene may itself be natural or synthetic, with the natural gene obtainable from cDNA or genomic libraries using degenerate probes based on the known amino acid sequence set forth in Julien et al., supra. Alternatively, polynucleotides may be synthesized based on the reported DNA sequence by well known techniques. For example, single-stranded DNA fragments may be prepared by the phosphoramidite method described by Beaucage and Carruthers (1981) Tett. Letters 22:1859-1862. A double-stranded fragment may then be obtained by synthesizing the complementary strand and annealing the strands together under appropriate conditions or by adding the complementary strand using DNA polymerase with an appropriate primer sequence.

The natural or synthetic DNA fragments coding for the desired GAD protein or fragment will then be incorporated in DNA constructs capable of introduction to and expression in an in vitro mammalian cell culture. Usually, the DNA constructs will be capable of replicating in prokaryotic hosts in order to facilitate initial manipulation and multiplication of the construct. After a sufficient quantity of the construct has been obtained, they will be introduced and usually integrated into the genome of cultured mammalian or other eukaryotic cell lines.

DNA constructs suitable for introduction to bacteria or yeast will include a replication system recognized by the host, the GAD DNA fragment encoding the desired protein or polypeptide product, transcriptional and translational initiation and regulatory sequences joined to the 5'-end of the structural DNA sequence, and transcriptional and translational termination regulatory sequences joined to the 3'-end of the structural sequence. The transcriptional regulatory sequences will include a heterologous promoter which is recognized by the host.

Conveniently, available cloning vectors which include the replication system and transcriptional and translational regulatory sequences together with an insertion site for the GAD DNA sequence may be employed. For transformation of mammalian and other eukaryotic cell lines, co-transfection of the cell lines in the presence of suitable marker, such as the DHFR gene, may be employed. Transfection may also be accomplished using chemical or electroporation techniques.

The ligands of the present invention will be utilized in a substantially pure form, that is, typically being at least about 50% w/w (weight/weight) purity, as well as being substantially free from interfering proteins and contaminants. Preferably, the ligands will be isolated or synthesized in a purity of at least about 80% w/w and, more preferably in at least about 95% w/w purity. Using conventional protein purification techniques, homogeneous peptides of at least 99% w/w can be obtained. For example, the proteins may be purified by use of antibodies specific for the GAD polypeptides using immunoadsorbent affinity chromatography. Such affinity chromatography is performed by first linking the antibodies to a solid phase support and then contacting the linked antibodies with the source of the ligand polypeptides, e.g., lysates of CNS or pancreatic cells or cells which have been recombinantly modified to produce GAD, or of supernatants of cells which have been recombinantly modified to secrete GAD when cultured.

For use in purification, antibodies to GAD may be obtained by injecting GAD or GAD fragments into a wide variety of vertebrates in accordance with conventional techniques. Suitable vertebrates include mice, rats, sheep, and goats. Usually, the animals are bled periodically with successively bleeds having improved titer and specificity. The antigens may be injected intramuscularly, interperitoneally, subcutaneously, or the like. Usually, vehicles employed such as a complete or incomplete Freund's adjuvant. Preferably, monoclonal antibodies can be prepared by well-known techniques. In particular, monoclonal Fab fragments may be produced in *E. coli* by the method of Huse et al. (1989) Science 246:1275-1281.

The assays of the present invention will detect the presence of at least one of the two molecular weight forms of GAD in patient sera, and will preferably detect both forms. It has been found (as described in the Experimental section hereinafter), that diabetic and prediabetic patients will usually have autoantibodies to both molecular weight forms of GAD, but in some cases will only have antibodies to either the higher molecular weight form or the lower molecular weight form. Thus, the preferred assay of the present invention will be able to detect the presence of antibodies reactive with either of the molecular weight forms of GAD, even in the absence of antibodies to the other molecular weight form.

Even more preferably, the assays of the present invention will be able to separately detect the presence of autoantibodies to each of the two molecular weight forms of GAD. It is believed that the pattern of antibodies present (i.e., only to the higher molecular weight GAD, only to the lower molecular weight GAD, or to both the molecular weight forms of GAD) will be a significant diagnostic indicator of the diseased state.

Assays for the separate detection of higher molecular weight GAD and of lower molecular weight GAD may conveniently be run by reacting the patient sera separately with each form of GAD, where the other form is substantially absent. The use of recombinantly produced GAD (or GAD fragments or analogs) will be particularly useful for performing separate detections since the GAD so produced will be free from the other molecular weight form.

In many cases, however, it will still be desirable to screen patient sera for the presence of both molecular weight forms of GAD simultaneously. A negative result (i.e., no reaction) will indicate that the patient is neither diabetic or prediabetic. A positive result will indicate that the patient is diabetic or prediabetic. The patient sera can then be further screened for the presence of each autoantibody separately, if desired. Simultaneous screening can conveniently be accomplished either with combinations of the two molecular weight forms of GAD which are isolated together from animal sources, or by combining separately produced recombinant GAD of each molecular weight form.

Assays according to the present invention typically rely on exposing the purified ligand(s) to a serum sample and detecting specific binding between the ligand and autoantibodies for the 64 kD pancreatic β-cell autoantigen which may be present in the serum. Binding between the autoantibodies and purified ligand indicates that the autoantibodies are present and is diagnostic of a diabetic or prediabetic condition in the patient. Alternatively, such assays can be used to monitor the condition of a patient who has undergone a pancreatic islet cell transplant, where the presence of the 64 k autoantibodies indicates an adverse immune response to the transplanted cells. The particular assay protocol chosen is not critical, and it is necessary only that the assay be sufficiently sensitive to detect a threshold level of the autoantigen which is considered to be positive.

Assays according to the present invention will be useful for identifying patients who are either prediabetic, i.e., who have circulating autoantibodies to the 64 kD autoantigen but who have not yet suffered sufficient damage to the insulin-producing β-cell to be clinically identified as having IDDM, or who suffer from clinical IDDM. The assays will also be useful for monitoring the effect of immunotherapy (as described hereinafter) to block or prevent autoimmune reactions to the β-cell and for monitoring the progress of the disease from pre-diabetes to clinical diabetes and will be particularly useful for monitoring the status of transplanted pancreatic β-cells in diabetic patients who have undergone an islet cell graft.

Suitable assays include both solid phase (heterogeneous) and non-solid phase (homogeneous) protocols. The assays may be run using competitive or non-competitive formats, and using a wide variety of labels, such as radioisotopes, enzymes, fluorescers, chemiluminescers, spin labels, and the like. A majority of suitable assays rely on heterogeneous protocols where the ligand is bound to a solid phase which is utilized to separate the ligand-autoantibody complex which forms when autoantibody is present in the serum sample. A particular advantage of using a purified ligand is that it facilitates the preparation of a solid phase for use in the assay. That is, the ligand may be conveniently immobilized on a variety of solid phases, such as dipsticks, particulates, microspheres, magnetic particles, test tubes, microtiter wells, and the like.

The solid phase is exposed to the serum sample so that the autoantibody, if any, is captured by the ligand. By then removing the solid phase from the serum sample, the captured autoantibodies can be removed from unbound autoantibodies and other contaminants in the serum sample. The captured autoantibody may then be detected using the non-competitive "sandwich" technique where labelled ligand for the autoantibody is exposed to the washed solid phase. Alternatively, competitive formats rely on the prior introduction of soluble, labelled autoantibody to the serum sample so that labelled and unlabelled forms may compete for binding to the solid phase. Such assay techniques are well known and well described in both the patent and scientific literature. Exemplary immunoassays which are suitable for detecting the autoantibodies in serum include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, the disclosures of which are incorporated herein by reference.

Particularly preferred are sensitive enzyme-linked immunosorbent assay (ELISA) methods which are described in detail in U.S. Pat. Nos. 3,791,932; 3,839,153; 3,850,752; 3,879,262; and 4,034,074. Such ELISA assays can provide measurement of very low titers of the autoantibodies.

According to the preferred ELISA technique, the purified ligand is bound either covalently or non-covalently to a solid surface. The solid surface is exposed to the serum sample where autoantibody present in the sample is captured and bound. Typically, the ligand on the solid phase will be present in excess so that the entire quantity of autoantibody may be bound. After separating the solid phase and washing its surface, the solid phase can be exposed to labelled reagent capable of specifically binding the captured autoantibody. The labelled reagent may be labelled purified ligand, or may be other ligand capable of binding to the autoantibody, e.g., labelled anti-human antibody. In this way, label is bound to the solid phase only if autoantibody was present in the serum sample. The enzyme labels may be detected by conventional visualization techniques, e.g., production of a colored dye, chemiluminescence, fluorescence, or the like.

A second preferred embodiment comprises radioimmunoassays (RIA) which are performed using a solid phase which has been prepared as described above. The solid phase is exposed to the serum sample in the presence of radiolabelled autoantibodies which can compete for binding to the immobilized ligand. In this way, the amount of radiolabel bound to the solid phase will be inversely proportional to the amount of autoantibodies initially present in the serum sample. After separation of the solid phase, non-specifically bound radiolabel can be removed by washing, and the amount of radiolabel bound to the solid phase determined. The amount of bound radiolabel, in turn, can be related to the amount of autoantibodies initially present in the sample.

Figure 3:
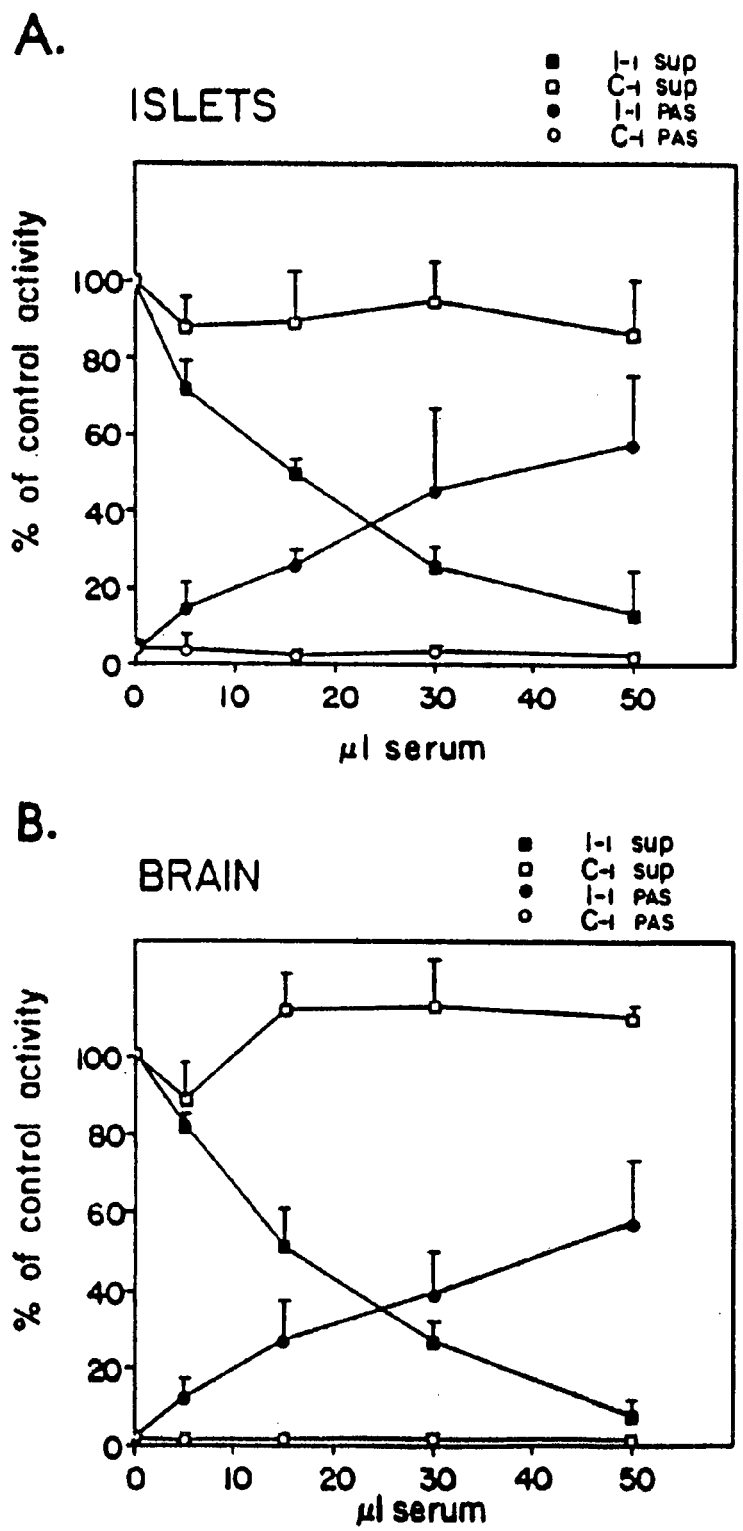
FIG. 3 includes two plots demonstrating that glutamic acid decarboxylase enzyme activity is inhibited in islet cell and brain cell lysates by immunoprecipitation with 64 k antibody positive sera.
Figure 4A:
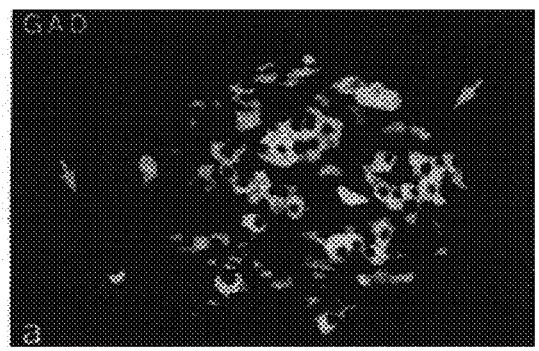
FIG. 4 is an immunofluorescence micrograph demonstrating the presence of glutamic acid decarboxylase in rat pancreatic β-cell islets.
Figure 4B:
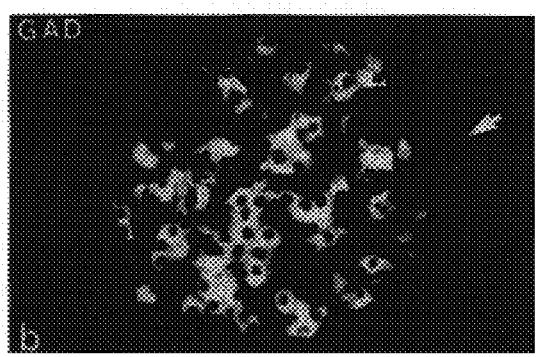
Figure 4C:
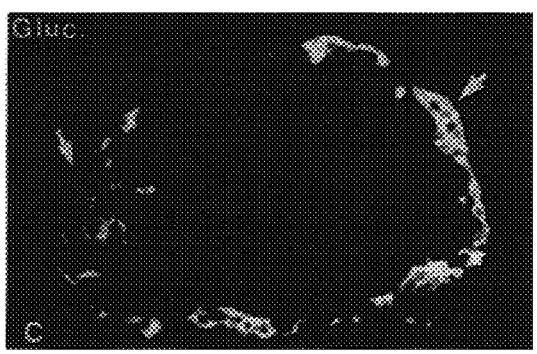
Figure 4D:
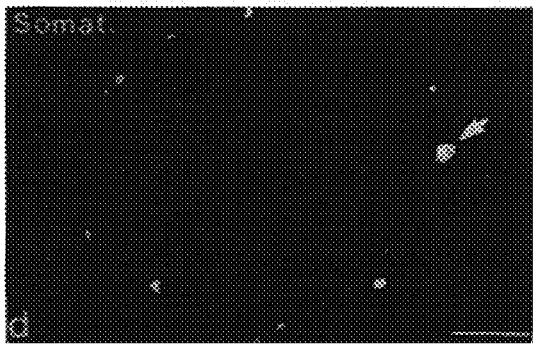

In addition to conventional immunological assay protocols as described above, the presence of the 64 k autoantibody in sera may be detected by measuring the effect of the autoantibody on the enzyme activity of lower molecular weight CNS GAD or pancreatic GAD introduced to a sample of the sera. Such direct enzyme assays may be based on the method described by Albers and Brady (1959) J. Biol. Chem. 234: 926-928, the disclosure of which is incorporated herein by reference. A detailed description of a suitable technique is presented hereinafter with reference to FIG. 3 in the Experimental section, wherein interaction between the autoantibodies and the GAD is detected based on loss of enzyme activity.

Purified ligand of the present invention can be incorporated as components of pharmaceutical compositions useful to attenuate, inhibit, or prevent the destruction of pancreatic β-cells associated with the onset of insulin-dependent diabetes mellitus. The compositions should contain a therapeutic or prophylactic amount of at least one purified ligand according to the present invention in a pharmaceutically-acceptable carrier. The pharmaceutical carrier can be any compatible, non-toxic substance suitable to delivery the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions. Such compositions can contain a single polypeptide or may contain two or more polypeptides according to the present invention in the form of a "cocktail."

It is presently believed by the inventors herein that the destruction of pancreatic β-cells in IDDM is a cellular autoimmune response. Thus, the pharmaceutical compositions should be suitable for inhibiting such a response. In particular, it may be desirable to couple the purified ligands of the present invention to immunoglobulins, e.g., IgG, or to lymphoid cells from the patient being treated in order to promote tolerance. Such an approach is described in Bradley-Mullen, *Activation of Distinct Subsets of T Suppressor Cells with Type III Pneumococcal Polysaccharide Coupled to Syngeneic Spleen Cells*, in: IMMUNOLOGICAL TOLERANCE TO SELF AND NON-SELF, Buttisto et al., eds., Annals N.Y. Acad. Sci, Vol. 392, pp 156-166, 1982. Alternatively, the peptides may be modified to maintain or enhance binding to the MHC while reducing or eliminating binding to the associated T-cell receptor. In this way, the modified GAD peptides may compete with natural GAD to inhibit helper T-cell activation and thus inhibit the immune response. In all cases, care should be taken that administration of the pharmaceutical compositions of the present invention does not potentiate the autoimmune response.

The pharmaceutical compositions just described are useful for parenteral administration. Preferably, the compositions will be administered parenterally, i.e., subcutaneously, intramuscularly, or intravenously. Thus, the invention provides compositions for parenteral administration to a patient, where the compositions comprise a solution or dispersion of the polypeptides in an acceptable carrier, as described above. The concentration of the protein or polypeptide in the pharmaceutical composition can vary widely, i.e., from less than about 0.1% by weight, usually being at least about 1% by weight to as much as 20% by weight or more. Typical pharmaceutical compositions for intramuscular injection would be made up to contain, for example, 1 ml of sterile buffered water and 1 to 100 μg of the purified ligand of the present invention. A typical composition for intravenous infusion could be made up to contain 100 to 500 ml of sterile Ringer's solution and 100 to 500 mg of the purified ligand. Actual methods for preparing parenterally administrable compositions are well known in the art and described in more detail in various sources, including, for example, *Remington's Pharmaceutical Science,* 15th Edition, Mack Publishing Company, Easton, Pa. (1980), which is incorporated herein by reference.

The pharmaceutical polypeptide compositions of the present invention may be administered for prophylactic treatment of prediabetic individuals identified by the assay methods of the present invention or for therapeutic treatment of individuals suffering from insulin-dependent diabetes mellitus but having a substantial residual mass of pancreatic β-cells. For therapeutic applications, the pharmaceutical compositions are administered to a patient suffering from established diabetes in an amount sufficient to inhibit or prevent further β-cell destruction. For individuals susceptible to diabetes, the pharmaceutical composition are administered prophylactically in an amount sufficient to either prevent or inhibit immune destruction of the β-cells. An amount adequate to accomplish this is defined as a "therapeutically-effective dose." Such effective dosage will depend on the severity of the autoimmune response and on the general state of the patient's health, but will generally range from about 1 to 500 mg of purified ligand per kilogram of body weight, with dosages of from about 5 to 25 mg per kilogram being more commonly employed.

The therapeutic methods of the present invention comprise administering the pharmaceutical compositions of the present invention in the amounts and under the circumstances described above.

In addition to using the GAD peptides and equivalent ligands directly in pharmaceutical compositions, it is also possible to use the GAD peptides and ligands to enhance tolerance to the 64 k autoantigen in diabetic and prediabetic individuals. Peripheral blood lymphocytes are collected from the individual in a conventional manner and stimulated by exposure to the GAD peptide or equivalent ligand, as defined above. Usually, other mitogens and growth enhancers will be present, e.g., phytohemagglutinin, interleukin 2, and the like. Proliferating T-helper cells may be isolated and cloned, also under the stimulation of GAD peptide or equivalent ligand. Clones which continue to proliferate may then be used to prepare therapeutic compositions for the individual. The cloned T-cells may be attenuated, e.g., by exposure to radiation, and administered to the host in order to induce tolerance. Alternatively, the T-cell receptor or portions thereof may be isolated by conventional protein purification methods from the cloned T-cells and administered to the individual. Such immunotherapy methods are described generally in Sinha et al. (1990) Science 248:1380-1388, the disclosure of which is incorporated herein by reference.

In some cases, after a T-helper cell has been cloned as described above, it may be possible to develop therapeutic peptides from the T-cell receptor, where the peptides would be beneficial for treating a population of diabetic and/or prediabetic individuals. In such cases, the T-cell receptor gene may be isolated and cloned by conventional techniques and peptides based on the receptor produced by recombinant techniques as described above. The recombinantly-produced peptides may then be incorporated in pharmaceutical compositions as described above.

The following examples are offered by way of illustration, not by way of limitation.

EXPERIMENTAL

Antibodies to GAD Immunoprecipitate the 64 kD Autoantigen from Islets

We first assessed whether serum S3, a sheep antiserum raised to purified rat brain GAD (Oertel et al. (1980) Brain Res. Bull. 5(Suppl 2):713-719), and sera from stiff man syndrome (SMS) patients positive for GAD antibodies (Solimena et al. (1988) supra. and Solimena et al. (1990) supra.) could immunoprecipitate the 64 kD autoantigen from rat islets. For this purpose we used $^{35}$S-methionine labelled rat islet cell fractions partially enriched for the 64 kD antigen (S-100 DP, FIG. 1). The GAD antibody positive sera immunoprecipitated a doublet of $^{35}$S-methionine labelled proteins, which on SDS-PAGE are of identical mobility to the 64 kD α/β autoantigen immunoprecipitated by IDDM sera (FIG. 1A, lanes 2-9).

To assess the possible common identity of the proteins recognized by the 64 kD antibody positive sera and by the GAD antibody positive sera, supernatants resulting from immunoprecipitation with GAD antibody positive sera were subsequently reprecipitated with 64 kD antibody positive IDDM sera. Similarly, supernatants resulting from immunoprecipitation with 64 kD antibody positive IDDM sera were reprecipitated with GAD antibody positive sera. Results from those experiments showed that GAD antibody positive sera, and 64 kD antibody positive sera each quantitatively removed the protein recognized by the other group of sera, demonstrating complete cross-reactivity between GAD and 64 kD antibody positive sera, and strongly suggesting that the 64 kD protein is GAD in rat islets (FIG. 1A lanes 10-20).

Figure 1A:
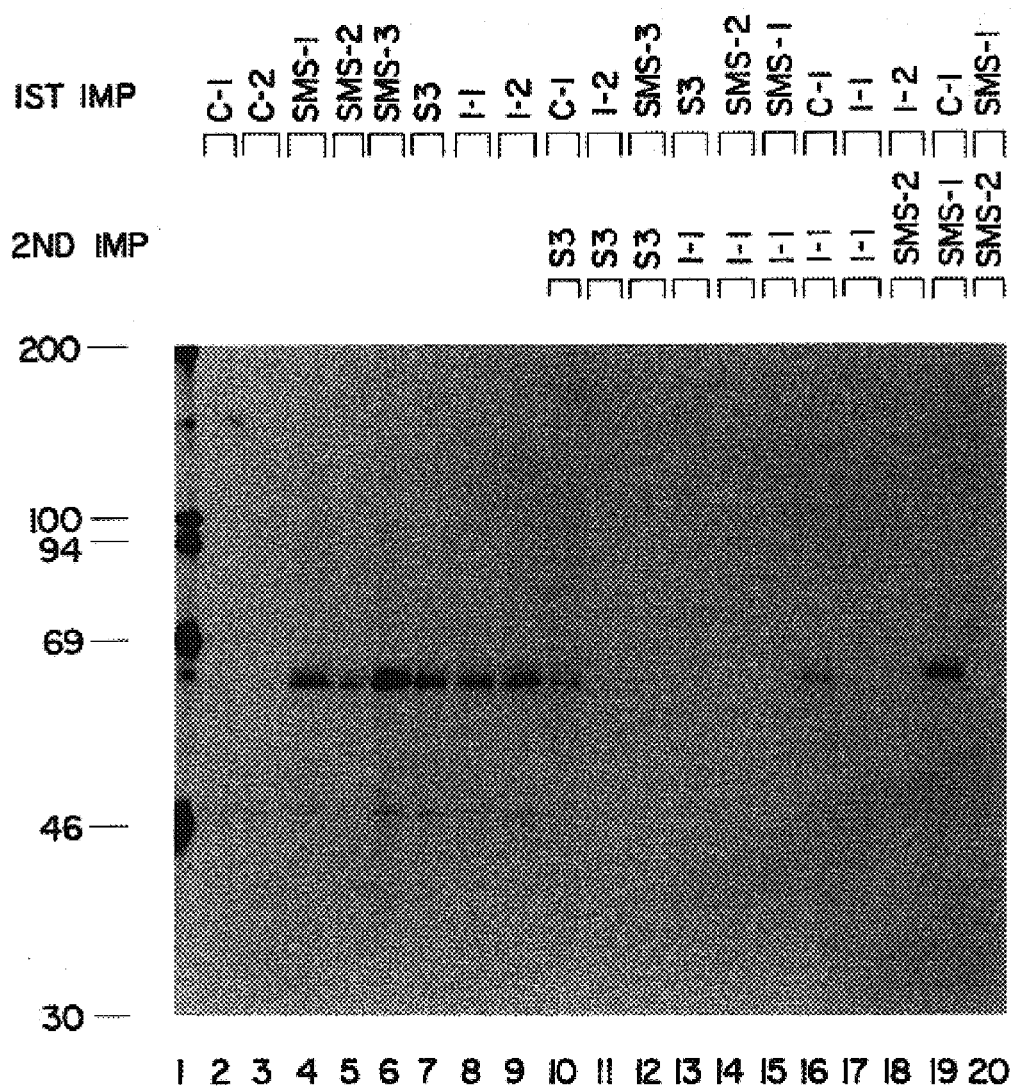
FIG. 1 includes a pair of fluorograms demonstrating that antibodies raised against glutamic acid decarboxylase and the 64 kD autoantibody obtained from diabetic sera recognize the same protein in rat islets.
Figure 1B:
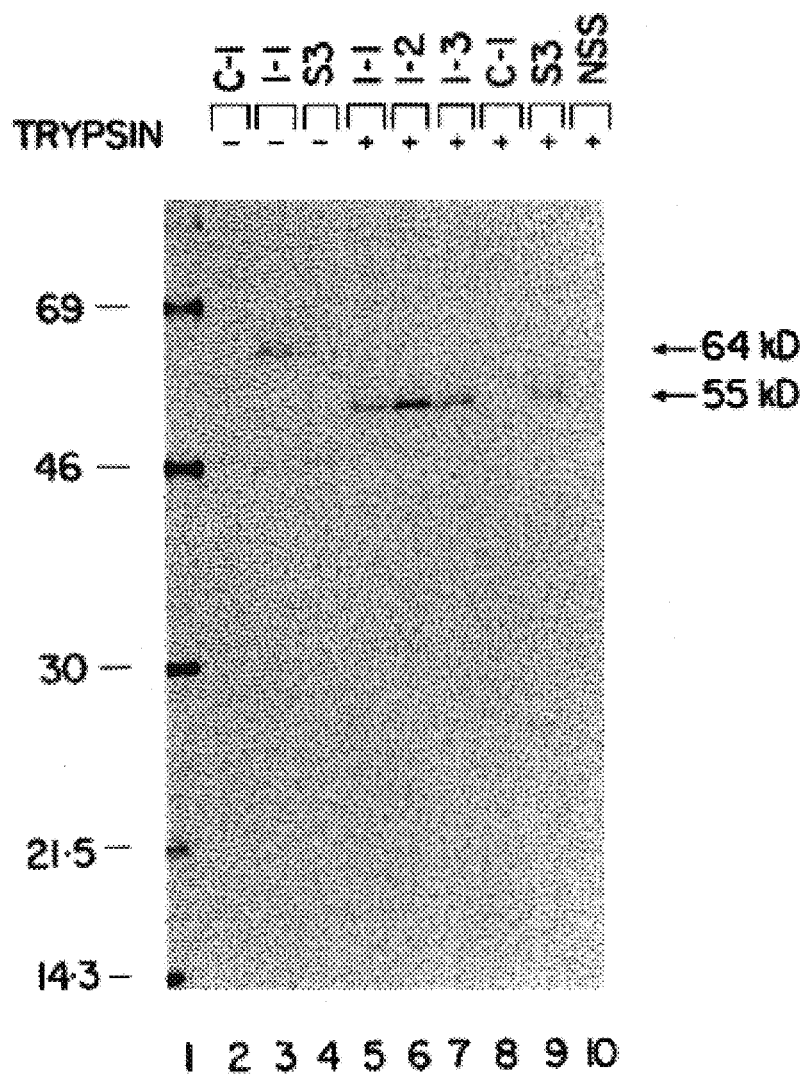

Trypsin digestion of $^{35}$S methionine labelled islet cell extracts followed by immunoprecipitation showed that a 55 kD immunoreactive fragment was formed both from the 64 kD protein and from GAD, further verifying their common identity (FIG. 1B). Furthermore, 2D analyses of GAD immunoprecipitated from $^{35}$S-methionine labelled islets with the S3 antiserum revealed an identical pattern to that described for the 64 kD protein (Baekkeskov et al. (1989) supra.) (results not shown). This pattern was also identical to the 2D pattern of pancreatic and brain GAD as demonstrated by Western blotting of 2D gels with the S3 serum (See FIG. 5A).

FIG. 1A is a fluorogram of an SDS-PAGE showing immunoprecipitation of Triton X-114 detergent phase purified soluble fractions from $^{35}$S-methionine labelled rat islets (S-100 DP) with GAD antibody positive sera, 64 kD antibody positive IDDM sera and control sera. Lanes 2-9, samples from a single immunoprecipitation with sera indicated at the top of each lane; lanes 10-20, samples from a second immunoprecipitation of supernatants remaining after a first immunoprecipitation. Sera used for first and second immunoprecipitations are indicated at the top of each lane. Sera used for the immunoprecipitations are indicated at the top of each lane. Sera used for the immunoprecipitations were: C, sera from healthy individuals; SMS, sera of SMS patients previously shown to be GAD antibody positive (Solimena (1990) supra.); 1, sera from newly diagnosed 64 kD antibody positive IDDM patients (Sigurdsson et al. *Genetic, Environmental and Autoimmune Etiology. Current Topics in Microbiology and Immunology* (eds. Baekkeskov et al.) Vol. 164 Springer, Verlag, Heidelberg, 1990) (numbers indicate patient code); S3, a sheep antiserum raised to purified rat brain GAD (Oertel et al. (1980) supra.). Molecular weight markers are shown in lane 1. The GAD antibody positive sera immunoprecipitate GAD from supernatants after immunoprecipitation with 64 kD antibody positive sera (lanes 11 and 18). The 64 kD antibody positive sera immunoprecipitate the 64 kD protein from supernatants after immunoprecipitation with control serum (lane 16), but not from supernatants after immunoprecipitation with GAD antibody positive sera (lanes 13-15). The triple band represents the 65 kD form and 64 kD α and β forms of the 64 kD autoantigen (Baekkeskov et al. (1989) supra.). SMS sera 1, 2, and 3 correspond to patients #190, 188 and 1 (Solimena et al. (1990) supra.).

FIG. 1B is a fluorogram showing immunoprecipitation of the 64 kD protein and GAD from S-100 DP of $^{35}$S-methionine labelled rat islets before (lanes 2-4) and after (lanes 4-10) trypsin digestion. Serum codes are as in legend for A. NSS is a preimmune sheep serum. Trypsin digestion results in a 55 kD immunoreactive fragment that is recognized by both 64 kD antibody positive sera and the GAD antibody positive serum S3.

Neonatal rat islets were isolated and labelled with $^{35}$S-methionine as described (Baekkeskov et al. (1989) supra.). Islets were swollen on ice for 10 min. in 10 mM Hepes pH 7.4, 1 mM $MgCl_2$ and 1 mM EGTA (HME buffer) and then homogenized by 20 strokes in a glass homogenizer. The homogenate was centrifuged at 2000 g to remove cell debris and the postnuclear supernatant centrifuged at 100,000 g for 1 hour to obtain a cytosol (S-100) and a particulate (P-100) fraction. Amphophilic proteins were purified from the S-100 fraction by a modification of the method described in Bordier, C. (1981) J. Biol. Chem. 256:1604-1607 for Triton TX-114 phase separation. In short, the S-100 fraction was made 1% in TX-114, warmed at 37° C. for 2 min to induce TX-114 phase transition, and centrifuged at 15,000 g for 2 min to separate the aqueous and detergent phases. The detergent phase was diluted in 20 mM Tris pH 7.4, 150 mM NaCl (TBS) and immunoprecipitated as described (Baekkeskov et al. (1989) supra.) using DP from 300 islets for each immunoprecipitate. Immunoprecipitates were analyzed by SDS-PAGE (10%) and processed for fluorography (Baekkeskov et al. (1981) Proc. Natl. Acad. Sci. USA 78:6456-6460). For the trypsin digestion S-100 DP from 4000 islets was diluted to 200 µl 10 mM Hepes, 5 mM EDTA, 5 mM pyrophosphate, 5 mM benzamidine/HCl, pH 7.5. Digested and undigested material was immunoprecipitated and the immunoprecipitants analyzed by SDS-PAGE (15%). Molecular weight markers shown are $^{14}$C methylated β-phosphorylase (MW 94,000 and 100,000), bovine serum albumin (MW 69,000), ovalbumin (MW 45,000) and carbonic anhydrase (MW 30,000). 64 kD antibody positive sera were from 3 newly diagnosed IDDM patients, control sera were from 2 healthy individuals, SMS sera were from 3 GAD antibody positive individuals (Solimena et al. (1990) supra.). The S3 antiserum was obtained from Dr. I. J. Kopin, NIH.

Autoantibodies to the 64 kD Protein Immunoprecipitate Gad from Brain and Islets.

Figure 2:
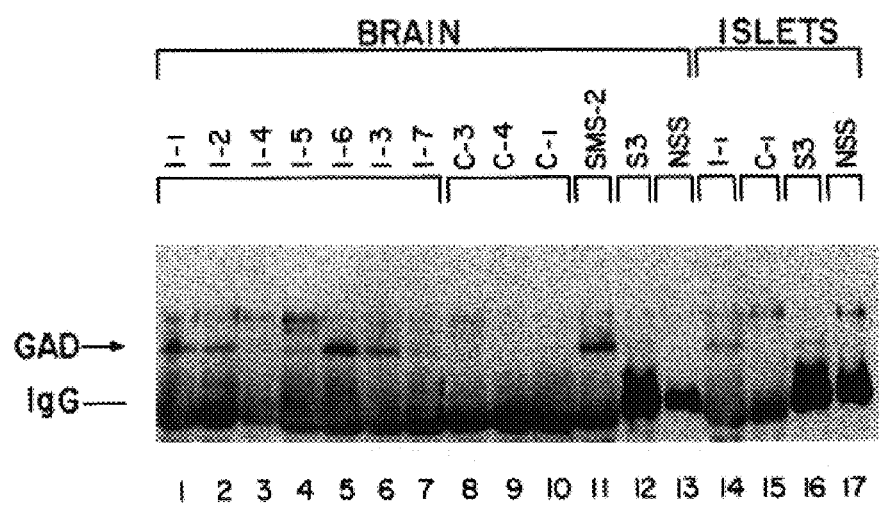
FIG. 2 is a Western blot of immunoprecipitates from rat brain and rat islet cells obtained by reaction with 64 k antibody positive sera and glutamic acid decarboxylase antibody positive sera.

We next analyzed whether 64 kD antibody positive sera could immunoprecipitate GAD from rat brain and islets. Membrane and soluble fractions were prepared from brain and islets and subjected to immunoprecipitation with serum S3, GAD antibody positive SMS sera, 64 kD antibody positive IDDM sera, and control sera. Presence of GAD in the immunoprecipitates was analyzed by Western blotting. The blots were probed with serum S3 or serum 7673, a rabbit serum raised to a synthetic 17 amino acid peptide corresponding to the C-terminus of the larger rat brain GAD isoform (Julien et al. (1990) supra.). Both sera gave identical results. FIG. 2 shows a Western blot containing some of such immunoprecipitates probed with serum S3. As expected, an immunoreactive band with the electrophoretic mobility of GAD was detected in immunoprecipitates obtained with GAD antibody positive sera (FIG. 2 lanes 11, 12, and 16). A band of identical mobility was visualized in all immunoprecipitates obtained with 64 kD antibody positive sera (7/7) (FIG. 2 lanes 1-7 and 14), but not in those obtained with control sera (FIG. 2) lanes 8-10, 13, 15, and 17). These results demonstrate that the protein immunoprecipitated from brain and islets by 64 kD antibody positive sera is indistinguishable from GAD.

FIG. 2 is a Western blot of immunoprecipitates of rat brain (S-100 DP) and islet cell (P-100 DP) fractions obtained with 64 kD antibody positive sera and GAD antibody positive sera. The blot was probed with the S3 serum. Sera used for the immunoprecipitation are indicated at the top of each lane by the same codes as in FIG. 1. The 64 kD protein immunoprecipitated from both brain and islets is immunostained by GAD antibodies. In the gel shown GAD migrated as a single band.

Neonatal rat brain was homogenized at 4° C. in seven volumes of HME buffer followed by centrifugation at 100,000 g for 1 h to obtain a soluble (S-100) and particulate (P-100) fractions. S-100 DP was prepared and aliquots ($^1/_{13}$ brain per lane) immunoprecipitated as described in the legend to FIG. 1. P-100 was prepared from neonatal rat islets and extracted in 200 ml TBS with 1% Triton X-114 for 2 h at 4° C. (Baekkeskov et al. (1989) supra.). P-100 DP was prepared as described for S-100 DP and aliquots (1500 islets per lane) immunoprecipitated. Immunoprecipitates were subjected to SDS-PAGE followed by electroblotting to a PVDF membrane (Immobilon®) (Towbin et al. (1979) Proc. Natl. Acad. Sci. USA 76:4850-4854), probing with the S3 serum and visualization by alkaline phosphatase conjugated rabbit anti sheep IgG.

The 64 kD Protein has GAD Enzyme Activity.

The implication that the 64 kD autoantigen is in fact GAD predicts that the 64 kD protein should have the enzymatic properties of GAD, and this possibility has been examined. We investigated whether GAD enzyme activity could be removed from neonatal rat islet and brain cell lysates by immunoprecipitation with a 64 kD antibody positive IDDM serum, and whether GAD activity could then be measured in the immunoprecipitates. Brain and islets cell fractions were subjected to immunoprecipitation with increasing amounts of a 64 kD antibody positive IDDM serum and the GAD enzyme activity was measured after immunoprecipitation in both supernatants and pellets (FIGS. 3A and B). The results demonstrated that immunoprecipitation with increasing amounts of 64 kD antibody positive serum but not with control serum removed the GAD activity from both brain and islet cell lysates in a dose-dependent manner and that in parallel, increasing amounts of GAD activity appeared in the immunoprecipitates. The GAD activity recovered in the immunoprecipitates did not account for all the activity lost from the supernatants, probably due to an inhibiting effect of antibodies on enzyme activity. In the case of islet cell extracts obtained from $^{35}$S-methionine labelled islets, SDS-PAGE analysis revealed that the only islet cell protein specifically detected in the immunoprecipitates obtained with the 64 kD antibody positive IDDM serum was the 64 kD autoantigen (see FIG. 1). Thus, the GAD enzyme activity measured in immunoprecipitates obtained with the 64 kD antibody positive IDDM serum is a property of the 64 kD autoantigen.

FIG. 3A is a plot obtained by immunoprecipitating aliquots (700 islets per sample) of S-100 DP from neonatal rat islets with increasing amounts of the 64 kD positive IDDM serum 1-1 (closed symbols) or the control serum C-1 (open symbols). GAD activity was measured in supernatants after immunoprecipitation (squares) and in pellets (circles). The activity in the supernatants calculated as percentage of the activity in non-immunoprecipitated samples incubated with the same amount of control serum. The activity in the immunoprecipitates was calculated as percentage of the activity in samples incubated without serum. Values are mean of 3 experiments ± standard deviation. FIG. 3B is similar to FIG. 3A, except that aliquots of S-100 DP from neonatal rat brain were used instead of islet cell material.

S-100 DP was prepared from islets and brain as described in the legends to FIGS. 1 and 2, except that buffers were supplemented with 1 mM aminoethylisothiouronium bromide hydrobromide (AET) and 0.2 mM pyridoxal-5'-phosphate (PLP). S-100 DP was diluted 10 fold in 50 mM potassium phosphate pH 6.8, 1 mM AET, 0.2 mM PLP (buffer A) and incubated with the indicated amounts of sera in a total volume of 150 ml for 7 h at 4° C. Immunocomplexes were absorbed to 150 µl protein A-Sepharose beads (PAS, Pharmacia) and isolated by centrifugation. The supernatants were collected and centrifuged 3 times to remove traces of PAS. The PAS pellets were washed 5 times by centrifugation in buffer A. The enzyme activity in the PAS pellets and the supernatants were measured using a modified version of the assay first described in Albers et al. (1959) J. Biol. Chem. 234:926-928. Both PAS pellets and supernatants were transferred to 1.5 ml screw cap tubes. 20 µl 5 mM L-glutamate in buffer A and 0.4 µCi [1-$^{14}$C]-L-glutamate (59 mCi/mmol, Amersham) were added. The tubes were closed immediately with a cap containing Whatman filter paper soaked in 50 µl 1 M hyamine hydroxide in methanol and incubated for 2 h at 37° C. The filter paper was then removed and the absorbed $^{14}CO_2$ measured in a scintillation counter. The specific activity of GAD in homogenates of neonatal brain and islet cell material was similar (approximately 40-70 mU/g protein).

Comparative Analyses of Brain and β-Cell GAD.

Figure 5A:
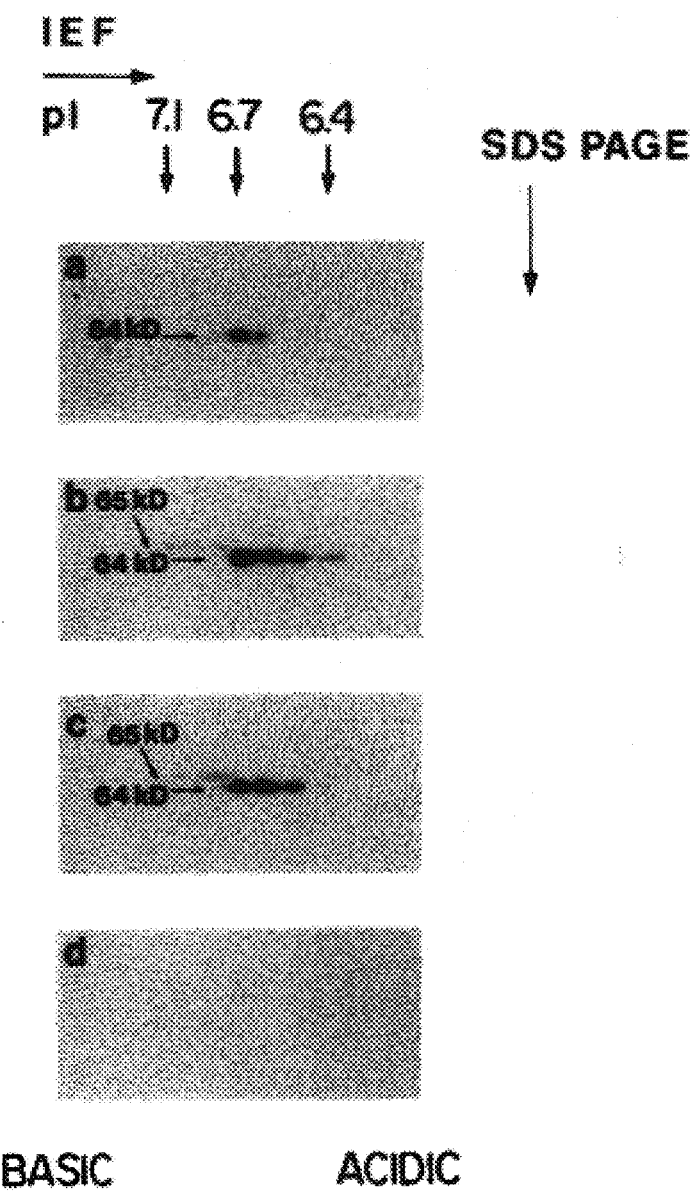
FIG. 5 includes a two-dimensional gel electrophoresis of the 64 kD autoantigen in rat brain and islet cells and a Western blot of soluble and particulate glutamic acid decarboxylase from rat brain and islets before and after trypsin digestion.
Figure 5B:
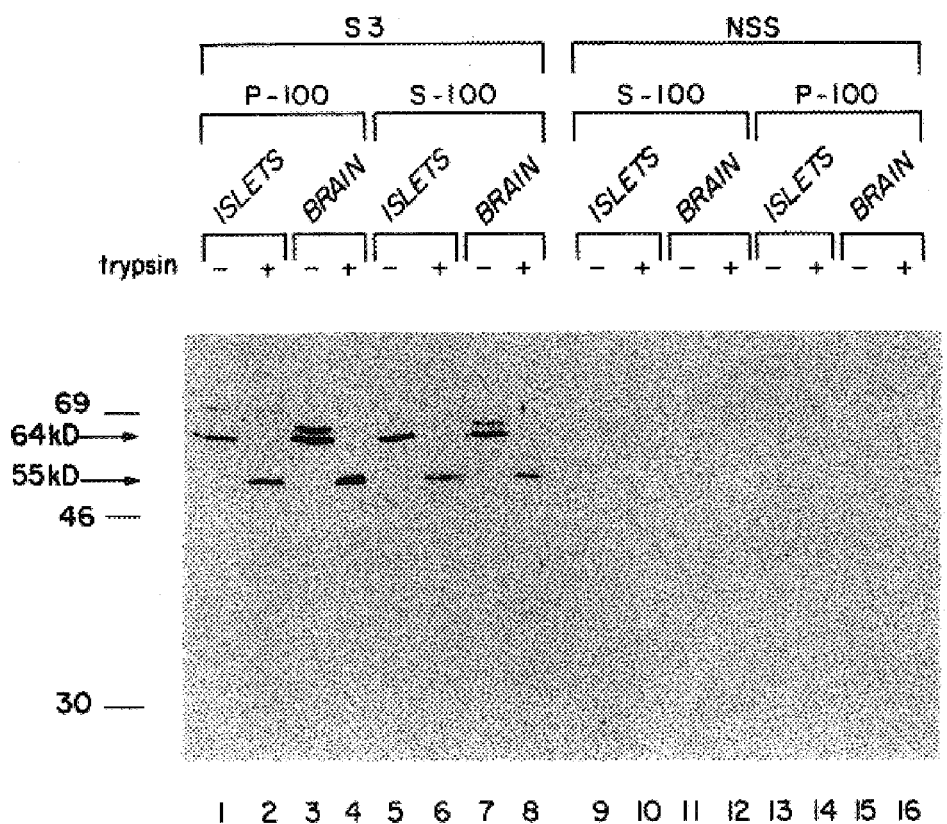

Analysis of GAD enzyme activity in neonatal and adult rat tissues showed that GAD is expressed at very high levels in brain and islet cells and is either absent from or present at very low levels in a variety of other tissues analyzed (results not shown) confirming previous reports (Erdo and Bowery (eds.) *GABAergic Mechanisms in the Mammalian Periphery*, New York, Raven Press (1986)). Within islets, double immunostaining with a monoclonal antibody to GAD and either glucagon or somatostatin confirmed the localization of GAD to the β-cell core, and the absence of GAD in the other endocrine cells, which are localized to the islet periphery (FIG. 4). GAD in brain and islets was found to have identical mobility by SDS-PAGE (FIG. 2) and by two dimensional gel electrophoresis using IEF/SDS-PAGE (FIG. 5A). We further compared the immunoreactive trypsin fragments generated from brain and islet GAD. Trypsin generated a 55 kD immunoreactive fragment from both islet and brain GAD (FIG. 5B, see also FIG. 1). In both tissues GAD was found in a soluble hydrophobic as well as a membrane bound hydrophobic forms (FIG. 5B) as described for the 64 kD islet cell autoantigen. The 65 kD component of the 64 kD protein was detected in brain and islet cells in some (FIG. 1A, FIG. 5A panels b and c, FIG. 5B and FIG. 6) but not in other analysis (FIG. 1B and FIG. 2). Furthermore the 64 kD α/β doublet was detected in some analysis (FIGS. 1A and 6). In sum the analyses of immunochemical and biochemical properties of the brain and islet GAD suggest that they are highly homologous.

FIG. 4 is an immunofluorescence micrograph showing pancreatic islets. The islet in panels a and c was double labelled for GAD and glucagon. The islet in panel b and d was double labelled for GAD and somatostatin. Arrows point to corresponding cells in the two pairs of panels. The β-cells in the central core of the islet, are brightly stained with the GAD antibody, while the glucagon and somatostatin positive cells do not stain with the same antibody.

Formaldehyde fixed frozen sections of rat pancreas were first rhodamine labelled for GAD using a mouse monoclonal GAD6, raised to purified rat brain GAD (Chang et al. (1988) supra.) and then fluorescein labelled for glucagon or somatostatin using rabbit polyclonal antibodies to either hormone and using methods described (Baumert et al. (1990) J. Cell Biol. 110:1285-1294). GAD6 was obtained from Dr. D. I. Gottlieb, University of Washington. Bar=25 mm.

FIG. 5A is a two-dimensional (2D) gel electrophoresis of neonatal rat and islet cell GAD/64 kD antigen. Panels a and b, Western blots of 2D gels of a neonatal islet particulate fraction (a) and a brain fraction (b) probed with the GAD antiserum S3; panels c and d, fluorograms of 2D gels of immunoprecipitates of a $^{35}$S-methionine labelled rat islets extract (S-100 DP) with the 64 kD antibody positive IDDM serum 1-1 (c) and with a control serum C-1 (d). The soluble fractions of brain and islets (panels b and c) contain both the 65 kD pI 7,1 component and the 64 kD pI 6,7 component. Both the 65 kD and the 64 kD component display charge heterogeneity previously described for the 64 kD autoantigen in islets (Baekkeskov et al. (1989) supra.). The panels both demonstrate the identical behavior of the 64 kD protein (panel c) and GAD (panels a and b) further proving they are the same protein and show the similarities of brain and islet GAD with regard to both charge and size.

FIG. 5B is a Western blot of soluble and particulate GAD obtained from neonatal rat brain and islets before and after trypsin digestion. Lanes 1-8, probing with S3 serum; lanes 9-16, probing with normal (preimmune) sheep serum. Trypsin digestion of both brain and islet GAD results in a 55 kD immunoreactive GAD fragment.

A particulate fraction was prepared from neonatal rat islet homogenates by centrifugation at 36,000 g (panel a). A low speed synaptosomal supernatant was prepared from brain as described (Huttner et al. (1983) J. Cell Biol. 96:1374-1388) (panel b). S-100 DP was prepared from neonatal rat islets and immunoprecipitated as described in the legend to FIG. 1 (panels c and d). Two-dimensional gel electrophoresis was performed as described by O'Farrell (1975) J. Biol. Chem. 250:4007-4021 and modified by Ames et al. (1976) Biochemistry 15:616-623. Immunoblotting was performed according to Towbin et al. (1979) supra. GAD in panels a and b was visualized by probing with the anti GAD serum S3, followed by rabbit anti sheep IgG serum and 1125 protein A and autoradiography. For the experiment in panel B, S-100 DP and P-100 DP from islets and brain were prepared as described in legends to FIGS. 1 and 2 and digested with trypsin as described in legend to FIG. 1. Brain and islet cell fractions were subjected to SDS-PAGE using 15% polyacrylamide gel. Western blotting and staining procedures were as described in legend to FIG. 2.

Comparison of GAD Antibodies in SMS and IDDM Sera.

The GAD reactivity in SMS sera has been demonstrated by Western blotting and by immunocytochemical staining of fixed tissue sections (Solimena et al. (1988) supra. and Solimena et al. (1990) supra.), i.e., assays that involve complete or partial denaturation of the antigen. The standard assay for 64 kD antibodies in IDDM sera has been immunoprecipitation from islet cell lysates prepared in non-denaturing conditions (Baekkeskov et al. (1987) J. Clin, Invest. 79:926-934, Baekkeskov et al. (1982) supra., and Baekkeskov et al. (1989) supra.). We selected sera from the individuals who had the highest immunoreactivity to the 64 kD autoantigen in immunoprecipitation experiments in a survey of 112 IDDM patients and prediabetic individuals without SMS (Sigurdsson et al. (1990) supra.) and tested them for immunoreactivity to the brain GAD protein on Western blots (5 sera) and for immunostaining of GABA-ergic neurons (7 sera). The results were compared with those for SDS sera. In contrast to the SMS sera, none of the IDDM sera detected the denatured GAD protein on Western blots (FIG. 6), and only one was able to weakly immunostain GABA-ergic neurons (FIG. 7 panel C). Titration of IDDM and SMS sera in immunoprecipitation experiments furthermore showed that SMS sera typically had 10-200 fold higher titer of GAD antibodies than IDDM sera (results not shown). In another survey of 74 IDDM patients, only three were found to be positive for antibodies to GABA-ergic neurons (FIG. 7, panel B) including the only two who were positive by Western blotting (13 and results not shown). In contrast, all SMS sera positive by immunochemistry and/or Western blotting were also positive by immunoprecipitation (results not shown).

Thus, in summary GAD antibodies in SMS patients are generally of a higher titer and distinct epitope recognition compared to GAD antibodies in IDDM patients. However, in rare cases GAD antibodies in IDDM patients may recognize denatured GAD. Interestingly, whereas the 7673 and S3 antisera recognize both the 65 kD and 64 kD α and β isoforms on Western blots (FIG. 6, lanes 2 and 4), human GAD autoantibodies as well as the monoclonal antibody GAD6 preferably recognize the smaller 64 kD α and β isoforms (FIG. 2, lanes 5 and 7-11). The GAD6 antibody was reported to be specific for the smaller GAD isoform in brain.

FIG. 6 illustrates Western blots of S-100 DP from neonatal rat brain (lanes 1-4) and 7-24) and islets (lanes 5 and 6) probed with GAD antibody positive SMS sera and sera from IDDM patients and prediabetic individuals with high immunoreactivity to the 64 kD/GAD protein in immunoprecipitation experiments. Sera are indicated at the top of each lane by the same codes as in FIG. 1. The S3 serum, 7673 serum, GAD6 serum and GAD antibody positive SMS sera recognize the denatured form of GAD in brain and islets, whereas the 64 kD positive IDDM sera do not. The S3 and 7673 sera react with both the 65 kD form and the 64 kD α and β forms, whereas GAD6 (previously shown to react selectively with the smaller brain GAD isoform (Chang et al. (1988) supra.) and the SMS sera only react with the 64 kD α and β components.

S-100 DP aliquots from rat brain and rat islets were subjected to SDS-PAGE, electroblotted and immunostained as described in legend to FIG. 2. Dilutions for immunostaining of Western blots were 1/200 for GAD6, 1/250 for IDDM sera, control human sera, SMS sera 2 and 5, the 7673 serum and normal rabbit serum, 1/500 for SMS sera 3 and 4 and 1/2000 for S3 and normal (preimmune) sheep serum. (SMS sera 4 and 5 correspond to patients #161 and 176 in Solimena et al. (1990) supra.).

Bright field light microscopy micrographs showing immunostaining of GABA-ergic nerve terminals in the rat cerebellar cortex with SMS and IDDM sera. Panel a, SMS-3 serum; panel b, IDDM serum 1-8 (patient 69 of Solimena et al. (1990) supra.); panel c, IDDM serum 1-2; panel d, IDDM serum 1-1. All sera, except 1-1, show the typical stain of GABA-ergic nerve terminals. Note the accumulation of immunoreactivity at the base of the Purkinje cells, where the GABA-ergic nerve endings of basket cells terminate. Procedures were carried out as described in Solimena et al. (1990) supra.

IDDM Patient Autoantibodies Recognize Both Molecular Weight Forms of Pancreatic Gad.

We cloned the higher molecular weight form of pancreatic GAD ($GAD_{67kD}$) from a rat islet cDNA library. By expressing this protein in a mammalian cell line (COS), we were able to produce $GAD_{67kD}$ that retained its enzymatic activity and was recognized by well characterized antibodies to brain GAD. We have used this cellular expression system to assess whether $GAD_{67kD}$ is a target of autoantibodies in IDDM and, if so, whether the antibodies occur with similar incidence as antibodies directed towards the lower molecular weight form of pancreatic GAD ($GAD_{64kD}$).

COS cells transfected with plasmids containing the cloned $GAD_{67kD}$ gene, and COS cells containing plasmids with the same gene inserted in a reverse direction (control) were cultured under standard conditions and labelled with $^{35}$S-methionine. Soluble hydrophilic proteins were isolated from the labelled cells (Baekkeskov et al. (1990) Nature 347:151-156), and immunoprecipitated with sera from 27 newly diagnosed IDDM patients, 15 prediabetic individuals (4 months to 7 years before clinical onset), 8 SMS patients, and 10 healthy individuals. 91.4% of all $GAD_{64kD}$ antibody positive sera from newly diagnosed IDDM patients and prediabetic individuals recognized $GAD_{67kD}$ (FIG. 7). Furthermore 2/5 (40%) $GAD_{64kD}$ antibody negative individuals were $GAD_{67kD}$ antibody positive. All the $GAD_{64kD}$ antibody negative control were also negative for $GAD_{67kD}$ antibodies. All SMS patients tested in the study, showed antibodies against both forms of GAD. The COS cells containing the $GAD_{67kD}$ gene inserted in the reverse direction did not contain any proteins that were specifically precipitated by IDDM sera.

We have thus demonstrated that the $GAD_{67kD}$ and $GAD_{64kD}$ antigens both contain epitopes recognized by antibodies associated with early and late phases of β-cell destruction. The high correlation between antibodies against $GAD_{64kD}$ and $GAD_{67kD}$ found in this study points to a high degree of homology between autoantigenic epitopes in the two forms of the enzyme. However, the data also indicates that the $GAD_{67kD}$ form contains distinct autoantigenic epitopes not present in the $GAD_{64kD}$ form and that testing for antibodies against both forms increases the sensitivity in newly diagnosed patients and prediabetic individuals.

Cloning of the rat islet $GAD_{67kD}$ was performed as follows. Four oligonucleotides matching sequences 128-151, 1112-1137 (reverse); 1035-1061 and 1883-1909 (reverse) of the published brain form of rat GAD cDNA (Julien et al. (1990) J. Neurochem. 54:703-705). They were used in combinations of two (128-151/1112-1137 and 1035-1061/1883-1909) in PCR reactions to amplify homologous sequences in cDNA from rat islets. The amplification products of each PCR reaction were then analyzed by agarose gel electrophoresis and the products within the size range expected were subsequently picked and amplified further with the appropriate primer pair to isolate individual PCR bands. We next asked whether any of these discrete bands consisted of a single DNA species, reflecting the amplification of part of the desired gene. The isolated molecules were digested with specific restriction enzymes. In most instances, the generated set of fragments had the size of the original brain cDNA. These PCR bands therefore each appear to contain a single cDNA species. To determine the nature of these cDNAs, an aliquot of the reaction was cloned into the plasmid vector Bluescript KS+, and colonies were screened with a probe consisting of a fragment from a cDNA clone of $GAD_{67kD}$ from rat brain obtained from Dr. A. Tobin of the University of California. Hybridizing colonies were subjected to PCR amplification, and only those giving a PCR product of the appropriate size were purified and further subjected to DNA sequence analysis. The sequence of each clone was completed with internal primers corresponding to nucleotides 500-516, 1305-1321 (antisense) and 1440-1556(antisense). PCR experiments using nested primers (standard primers followed by primers to internal sequences) were used to verify that fragments giving a positive signal were devoid of spurious molecules. The sequencing of the cDNAs showed a complete sequence homology with $GAD_{67kD}$ in brain. Thus, rat islet cells express a form of GAD which is identical to $GAD_{67kD}$. Based on those results and the comparative analysis of $GAD_{67kD}$ in brain and the 65 kD form in islets at the protein level, we conclude that the 65 kD β-cell is encoded by the $GAD_{67kD}$ gene.

Similar results were obtained with COS cells expressing human brain $GAD_{67kD}$ (higher molecular weight form) and $GAD_{65kD}$ (lower molecular weight form). cDNA clones isolated from a human brain cDNA library and encoding $GAD_{65kD}$ or $GAD_{65kD}$, obtained from Dr. Tobin, were inserted into a COS-cell expression vector 91023B (Wong et al. (1985) Science 228:810-815). COS7 cells were transfected using a lipofection reagent and labelled with $^{35}$S-methionine 48 hours after transfection. We used cell lysates from the COS transfection to analyze sera from 25 newly diagnosed IDDM patients, 14 prediabetic individuals, 8 SMS patients, and 10 controls. All of these sera (except for controls) had previously been found to contain antibodies to the amphiphilic 64 kD form of GAD using isolated islets as a source of antigen. All sera which were previously positive for the 64 kD islet cell form were also found to be positive for COS-cell $GAD_{65kD}$. Similarly, all sera negative for antibodies to the islet 64 kD form were negative for antibodies to COS-cell $GAD_{65kD}$, thereby confirming that GAD and the 64 kD islet cell form are antigenically identical. Although the majority of IDDM sera (18/25) and prediabetic sera (8/14) and all SMS sera (8/8) recognized both $GAD_{65}D$ and $GAD_{67kD}$, sera from a few IDDM patients recognized either $GAD_{65kD}$ (3/25) or $GAD_{67kD}$ (3/25) but not both forms. Furthermore, amongst the prediabetic individuals, 3 of 14 specifically recognized $GAD_{65kD}$ whereas none were specific for antibodies to $GAD_{67kD}$. We conclude that autoantibodies in both IDDM and SMS patients can recognize both forms of GAD in a native configuration and that some IDDM and prediabetic individuals can preferably recognize either one or the other form of GAD. The results in the prediabetic group suggest that antibodies may develop earlier to $GAD_{65kD}$ than to $GAD_{67kD}$.

Characterization of Pancreatic GAD and Comparison with CNS GAD.

We have identified two autoantigenic forms of GAD in rat pancreatic β-cells, a Mr 65000 ($GAD_{65kD}$) hydrophilic and soluble form of pI 6.9-7.1, and a Mr 64000 ($GAD_{64kD}$) component of pI 6.7. $GAD_{64kD}$ was found to be more abundant than $GAD_{65kD}$ and has three distinct forms with regard to cellular compartment and hydrophobicity. A major form of $GAD_{64kD}$ is hydrophobic and firmly membrane-anchored, and can only be released from membrane fractions by detergent. A second form is hydrophobic but soluble or of a low membrane avidity, and a third minor form is soluble and hydrophilic. All the GAD4 kD forms have identical pI and mobility on SDS-PAGE. Results of pulse chase labelling with $^{35}$S-methionine were consistent with $GAD_{64kD}$ being synthesized as a soluble protein that is processed into a firmly membrane anchored form in a process which involves increases in hydrophobicity but no detectable changes in size or charge. All the $GAD_{64kD}$ forms can be resolved into two isoforms, α and β, which differ by approximately 1 kDa in mobility on SDS-PAGE but are identical with regard to all other parameters analyzed in our study. $GAD_{65kD}$ has a shorter half-life than the $GAD_{64kD}$ forms, remains hydrophilic and soluble, and does not resolve into isomers. Comparative analysis of the brain (CNS) and β-cell forms of GAD showed that $GAD_{65kD}$ and $GAD_{64kD}$ in pancreatic β-cells correspond to the larger and smaller forms of GAD in brain respectively.

Although the foregoing invention has been described in detail for purposes of clarity of understanding, it will be obvious that certain modifications may be practiced within the scope of the appended claims.

What is claimed is:

1. A method for detecting autoantibodies to an approximately 64 kD pancreatic β-cell autoantigen in sera, said method comprising exposing a serum sample to glutamic acid decarboxylase (GAD) and detecting specific interaction between the GAD and the autoantibodies, wherein the GAD is expressed from a recombinant construct, prepared from the central nervous system or produced by solid-phase peptide synthesis.

2. A method as in claim 1, wherein the glutamic acid decarboxylase is prepared from a natural source.

3. A method as in claim 1, wherein the glutamic acid decarboxylase is expressed from a recombinant construct or by solid phase peptide synthesis.

4. A method as in claim 1, wherein the serum sample is combined with soluble, labeled autoantibodies so that labeled and unlabeled autoantibodies compete to form complexes with the GAD, whereby the amount of label bound in such complexes is inversely proportional to the concentration of autoantibodies initially present in the serum sample.

5. A method as in claim 4, wherein the autoantibodies are labeled with an enzyme and binding of the GAD to the autoantibodies inhibits enzyme activity.

6. A method as in claim 4, wherein the GAD is bound to a solid phase and the method further comprises removing the solid phase from the serum sample in order to separate labeled complexes from unbound, labeled autoantibodies.

7. A method as in claim 6, wherein the label present on the solid phase is measured.

8. A method as in claim 6, wherein the label remaining in the serum sample is measured.

9. A method as in claim 1, wherein the GAD is bound to a solid phase and the method further comprises separating the solid phase to remove substantially all autoantibodies present in the sample and measuring the amount of autoantibodies removed, whereby the amount is directly proportional to the concentration of autoantibodies present in the sample.

10. A method as in claim 9, wherein the amount of autoantibodies is measured by exposing the solid phase to labeled reagent specific for the autoantibodies and determining the amount of bound labeled reagent.

11. A method as in claim 1, wherein the GAD possesses glutamic acid decarboxylase activity and the interaction between the GAD and the autoantibodies is deduced based on loss of enzyme activity.

12. A method for screening for insulin dependent diabetes mellitus in a patient, said method comprising:
   obtaining a serum sample from the patient;
   exposing the serum sample to glutamic acid decarboxylase (GAD); and
   detecting interaction between the glutamic acid decarboxylase and autoantibodies which may be present in the serum sample, wherein such interaction indicates susceptibility or presence of insulin dependent diabetes mellitus,
   wherein the GAD is expressed from a recombinant construct, prepared from the central nervous system or produced by solid-phase peptide synthesis.

13. A method as in claim 12, wherein the glutamic acid decarboxylase is prepared from a natural source.

14. A method as in claim 12, wherein the glutamic acid decarboxylase is produced by expression from a recombinant construct or by solid phase peptide synthesis.

15. A method as in claim 12, wherein the serum sample is combined with soluble, labeled autoantibodies so that labeled and unlabeled autoantibodies compete to form complexes by binding to the purified glutamic acid decarboxylase, whereby the amount of label bound in such complexes is inversely proportional to the concentration of autoantibodies initially present in the serum sample.

16. A method as in claim 15, wherein the purified glutamic acid decarboxylase is bound to a solid phase and the method further comprises removing the solid phase from the serum sample in order to separate labeled complexes from unbound, labeled autoantibodies.

17. A method as in claim 16, wherein the label present on the solid phase is measured.

18. A method as in claim 16, wherein the label remaining in the serum sample is measured.

19. A method as in claim 12, wherein the purified glutamic acid decarboxylase is bound to a solid phase and the method further comprises separating the solid phase to remove substantially all autoantibodies present in the sample and measuring the amount of autoantibodies removed, whereby the amount is directly proportional to the concentration of autoantibodies present in the sample.

20. A method as in claim 19, wherein the amount of autoantibodies is measured by exposing the solid phase to labeled reagent specific for the autoantibodies and determining the amount of bound labeled reagent.

21. A method as in claim 12, wherein the purified glutamic acid decarboxylase possesses native enzyme activity and the interaction is deduced based on loss of enzyme activity.

22. A method as in claim 12, wherein the glutamic acid decarboxylase is bound to a solid phase and the interaction is detected by radioimmunoassay.

23. A method as in claim 12, wherein the glutamic acid decarboxylase is bound to a solid phase wherein the glutamic acid decarboxylase is bound to a solid phase.

24. The method of claim 1, wherein the GAD or fragment is at least 50% pure w/w.

25. A method for the early detection of the onset of insulin dependent diabetes, said method comprising the following steps:
   (a) contacting serum collected from a patient to be tested for insulin dependent diabetes with an entire recombinantly produced glutamic acid decarboxylase protein wherein said glutamic acid decarboxylase protein is capable of binding with 64K autoantibodies to form an immunocomplex comprising said glutamic acid decarboxylase protein bound to said 64K autoantibodies; and
   (b) detecting insulin dependent diabetes by determining whether any of said immunocomplex is formed.

26. The method, according to claim 25, wherein said glutamic acid decarboxylase protein is detectably labeled.

27. The method, according to claim 26, wherein said determining step comprises contacting immunocomplex, if present, with a detectably labeled protein capable of binding to the immunocomplex, and detecting the presence of said labeled immunocomplex.

28. The method, according to claim 27, wherein the detectably labeled protein is a labeled animal anti-human immunoglobulin.

29. A method for the early detection of the onset of insulin dependent diabetes, said method comprising the following steps:
   (a) contacting serum collected from a patient to be tested for insulin dependent diabetes with an entire mammalian glutamic acid decarboxylase protein wherein said glutamic acid decarboxylase protein is capable of binding with 64K autoantibodies to form an immunocomplex comprising said glutamic acid decarboxylase protein bound to said 64K autoantibodies, and wherein said glutamic acid decarboxylase protein is isolated from a non-human source; and
   (b) detecting insulin dependent diabetes by determining whether any of said immunocomplex is formed.

30. The method of claim 12, wherein the interaction between the glutamic acid decarboxylase and the autoantibodies indicates susceptibility to insulin dependent diabetes mellitus in the patient.

31. The method of claim 12, wherein the interaction between the glutamic acid decarboxylase and the autoantibodies indicates presence of insulin dependent diabetes mellitus in the patient.

32. The method of claim 12, wherein the interaction is detected by radioimmunoassay.

33. The method of claim 12, wherein the interaction is detected by isolating immune complexes formed from the glutamic acid decarboxylase and the autoantibodies by binding to protein A-agarose particles.

34. The method of claim 1, wherein the GAD is prepared by homogenizing rat brain cells, and centrifuging to produce a particulate fraction and a soluble fraction containing the GAD.

* * * * *